(12) United States Patent
Garcia-Blanco et al.

(10) Patent No.: US 11,807,853 B2
(45) Date of Patent: *Nov. 7, 2023

(54) SOLUBLE INTERLEUKIN-7 RECEPTOR (SIL7R) MODULATING THERAPY TO TREAT AUTOIMMUNE DISEASES AND CANCER

(71) Applicant: Board of Regents, The University of Texas System, Austin, TX (US)

(72) Inventors: Mariano A. Garcia-Blanco, Galveston, TX (US); Gaddiel Galarza-Munoz, Galveston, TX (US); Shelton S. Bradrick, Galveston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 131 days.

This patent is subject to a terminal disclaimer.

(21) Appl. No.: 17/411,265

(22) Filed: Aug. 25, 2021

(65) Prior Publication Data

US 2021/0403920 A1 Dec. 30, 2021

Related U.S. Application Data

(63) Continuation of application No. 17/027,467, filed on Sep. 21, 2020, now Pat. No. 11,118,186, which is a continuation of application No. PCT/US2019/023719, filed on Mar. 22, 2019.

(60) Provisional application No. 62/646,716, filed on Mar. 22, 2018.

(51) Int. Cl.
| | | |
|---|---|---|
| C12N 15/113 | (2010.01) | |
| A61K 31/7088 | (2006.01) | |
| A61K 45/06 | (2006.01) | |
| C12Q 1/68 | (2018.01) | |

(52) U.S. Cl.
CPC ...... *C12N 15/1138* (2013.01); *A61K 31/7088* (2013.01); *A61K 45/06* (2013.01); *C12N 2310/11* (2013.01); *C12N 2320/31* (2013.01); *C12N 2320/33* (2013.01)

(58) Field of Classification Search
None
See application file for complete search history.

(56) References Cited

U.S. PATENT DOCUMENTS

| | | |
|---|---|---|
| 5,693,773 A | 12/1997 | Kandimalla |
| 5,856,462 A | 1/1999 | Agrawal |
| 5,886,165 A | 3/1999 | Kandimalla |
| 5,929,226 A | 7/1999 | Padmapriya |
| 5,973,136 A | 10/1999 | Agrawal |
| 6,124,445 A | 9/2000 | Imbach |
| 6,127,533 A | 10/2000 | Cook |
| 6,140,482 A | 10/2000 | Iyer |
| 6,146,829 A | 11/2000 | Cook |
| 6,147,200 A | 11/2000 | Manoharan |
| 6,153,737 A | 11/2000 | Manoharan |
| 6,158,344 A | 12/2000 | Walker |
| 6,160,109 A | 12/2000 | Just |
| 6,160,152 A | 12/2000 | Capaldi |
| 6,166,188 A | 12/2000 | Cook |
| 6,166,197 A | 12/2000 | Cook |
| 6,172,209 B1 | 1/2001 | Manoharan |
| 6,175,004 B1 | 1/2001 | Ross |
| 6,194,598 B1 | 2/2001 | Cook |
| 11,118,186 B2 | 9/2021 | Garcia-Blanco et al. |
| 2005/0118605 A9 | 6/2005 | Baker |
| 2005/0143333 A1 | 6/2005 | Richards |

OTHER PUBLICATIONS

Allcock, et al., "The Central MHC Gene, BAT 1, May Encode a Protein That Down-Regulates Cytokine Production", Genes to Cell, 2001, 6, 487-494.

Anderson, et al., "Meta-analysis identifies 29 additional ulcerative colitis risk loci, increasing the number of confirmed associations to 47", Nature Genetics, vol. 43, No. 3, Mar. 2011.

Badot, et al., Rheumatoid arthritis synovial fibroblasts produce a soluble form of the interleukin-7 receptor in response to proinflammatory cytokines, J. Cell. Mol. Med., vol. 15, No. 11, 2011, pp. 2335-2342.

Badot, et al., "Serum soluble interleukin 7 receptor is strongly associated with lupus nephritis in patients with systemic lupus erythematosus", Open Access, Ann Rheum Dis 2013;72:453-456.

Barrett, et al., "Genome-wide association study and meta-analysis find that over 40 loci affect risk of type 1 diabetes", Nature Genetics, vol. 41, No. 6, Jun. 2009.

Bennett, et al. "Antisense oligonucleotides as a tool for gene functionalization and target validation" Biochimica et Biophysica Acta 1489 (1999) 19-30.

Cheong, et al., "Localization of Central MHC Genes Influencing Type I Diabetes", Elsevier, Human Immunology 62, 1363-1370 (2001).

Degli-Esposti, et al., "Ancestral Haplotypes Carry Haplotypic and Haplospecific Polymorphisms of BAT1: Possible Relevance to Autoimmune Disease", European Journal of Immunogenetics (1992), 19, 121-127.

(Continued)

*Primary Examiner* — Sean McGarry
(74) *Attorney, Agent, or Firm* — Edwin S. Flores; Daniel J. Chalker; Chalker Flores, LLP

(57) ABSTRACT

The present invention includes compositions and methods for treating an autoimmune disorder or a cancer in a subject in need thereof, the method comprising: administering an effective amount of a composition comprising an oligonucleotide that specifically binds a complementary sequence of the Interleukin-7 receptor (IL7R) pre-mRNA that influences splicing of exon 6, wherein the SM-ASO increases or decreases inclusion of exon 6 in IL7R pre-mRNAs and respectively decreases or increases expression of the soluble isoform of IL7R (sIL7R). In certain embodiments, the oligonucleotide is an antisense oligonucleotide (ASO), or a splice-modulating antisense oligonucleotide (SM-ASO).

21 Claims, 17 Drawing Sheets

Specification includes a Sequence Listing.

(56) References Cited

OTHER PUBLICATIONS

Evsyukova, et al., "Cleavage and polyadenylation specificity factor 1 (CPSF1) regulates alternative splicing of interleukin 7 receptor (IL7R) exon 6", RNA (2013), 19:103-115. Published by Cold Spring Harbor Laboratory.

Gaddiel Galarza-Munoz, et al., "Human Epistatic Interaction Controls IL7R Splicing and Increases Multiple Sclerosis Risk", Cell 169, 72-84, Mar. 23, 2017 ᵃ 2017 Elsevier Inc.

Gregory, et al., "Interleukin 7 receptor a chain (IL7R) shows allelic and functional association with multiple sclerosis", Nature Genetics, published online Jul. 29, 2007.

Kilding, et al., "Additional Genetic Susceptibility for Rheumatoid Arthritis Telomeric of the DRB1 Locus", Arthritis Rheumatism , vol. 50, No. 3, Mar. 2004, pp. 763-769.

Lauwerys, et al.,"sIL7R concentrations in the serum reflect disease activity in the lupus kidney", Biomarker Studies, Lupus Science Medicine 2014;1:e000036.

Lundstrom, et al., "Soluble IL7Ra potentiates IL-7 bioactivity and promotes autoimmunity", PNAS | Published online Apr. 22, 2013 | E1761-E1770.

Maraskovsky, et al., "Impaired survival and proliferation in IL-7 receptor-deficient peripheral T cells", The Journal of Immunology, 1996; 157:5315-5323.

McKay, et al., "Haplotypes of the interleukin 7 receptor alpha gene are correlated with altered expression in whole blood cells in multiple sclerosis", Genes and Immunity (2008) 9, 1-6.

Monti, et al., "Concentration and Activity of the Soluble Form of the Interleukin-7 Receptor a in Type 1 Diabetes Identifies an Interplay Between Hyperglycemia and Immune Function", Diabetes, vol. 62, Jul. 2013.

Nakamura, et al., "Genome-wide Association Study Identifies TNFSF15 and POU2AF1 as Susceptibility Loci for Primary Biliary Cirrhosis in the Japanese Population", The American Journal of Human Genetics 91, 721-728, Oct. 5, 2012.

Okamoto, et al., "Identification of IkBL as the Second Major Histocompatibility Complex-Linked Susceptibility Locus for Rheumatoid Arthritis", Am. J. Hum. Genet. 72:303-312, 2003.

Patermoster, "Meta-analysis of genome-wide association studies identifies three new risk loci for atopic dermatitis", Nature Genetics, vol. 44, No. 2, Feb. 2012.

Peschon, et al., "Early Lymphocyte Expansion Is Severely Impaired in Interleukin 7 Receptor-deficient Mice", J. Exp. Med., vol. 180, Nov. 1994, pp. 1955-1960.

Price, et al., "Polymorphisms at positions -22 and -348 in the promoter of the BAT1 gene affect transcription and the binding of nuclear factors", Human Molecular Genetics, 2004, vol. 13, No. 9, 967-974.

Puel, et al.,"Defective IL7R expression in T-B+NK+ severe combined immunodeficiency", Nature Genetics, vol. 20, Dec. 1998.

Quinones-Lombrana, et al., "BAT1 promoter polymorphism is associated with rheumatoid arthritis Susceptibility", The Journal of Rheumatology, 2008, 35, vol. 35, No. 5, 741-744.

Roifman, et al., "Apartial deficiency of interleukin-7Ra is sufficient to abrogate T-cell development and cause severe combined immunodeficiency", Immunobiology, Blood, Oct. 15, 2000 z vol. 96, No. 8.

Todd, et al., "Robust associations of four new chromosome regions from genome-wide analyses of type 1 diabetes", Nat. Genet., Jul. 2017; 39(7): pp. 857-864.

Wong, et al., "Alleles of the proximal promoter of BAT1, a putative anti-inflammatory gene adjacent to the TNF cluster, reduce transcription on a disease-associated MHC haplotype", Genes to Cells, (2003), 8, 403-412.

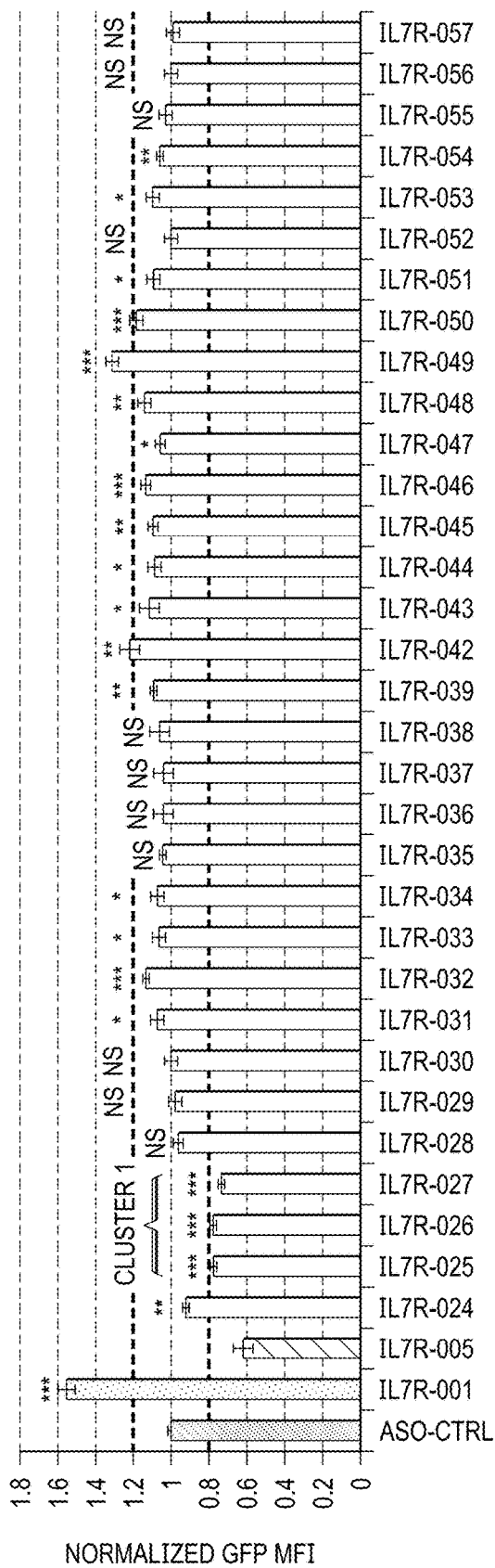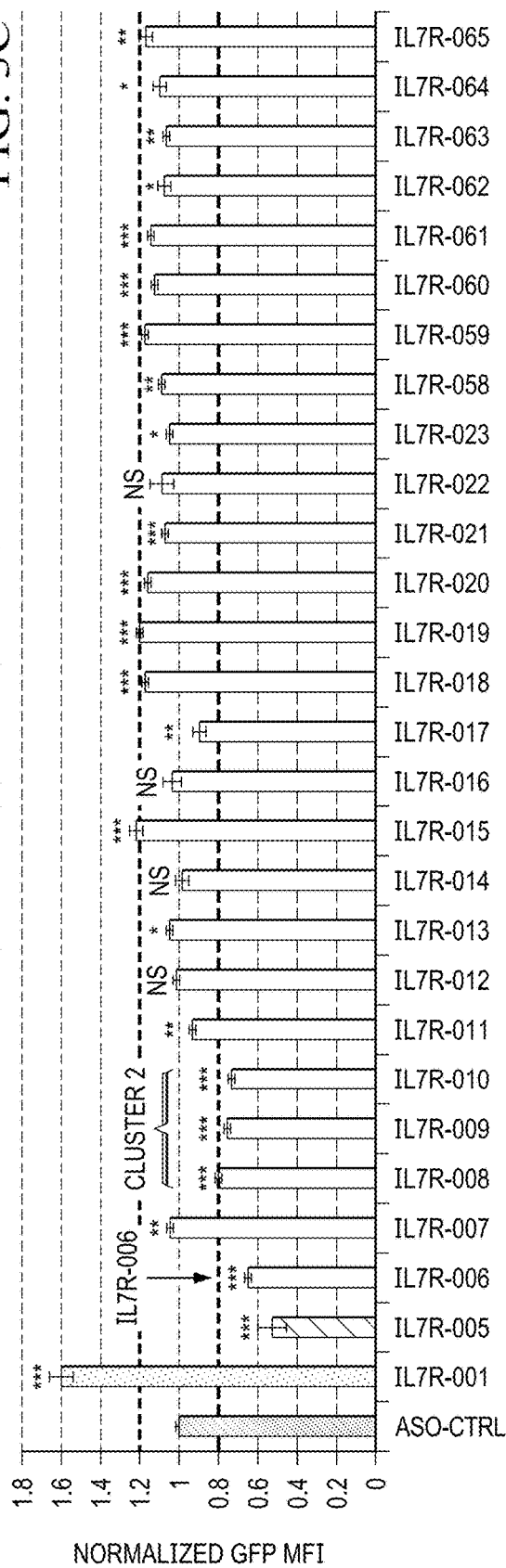

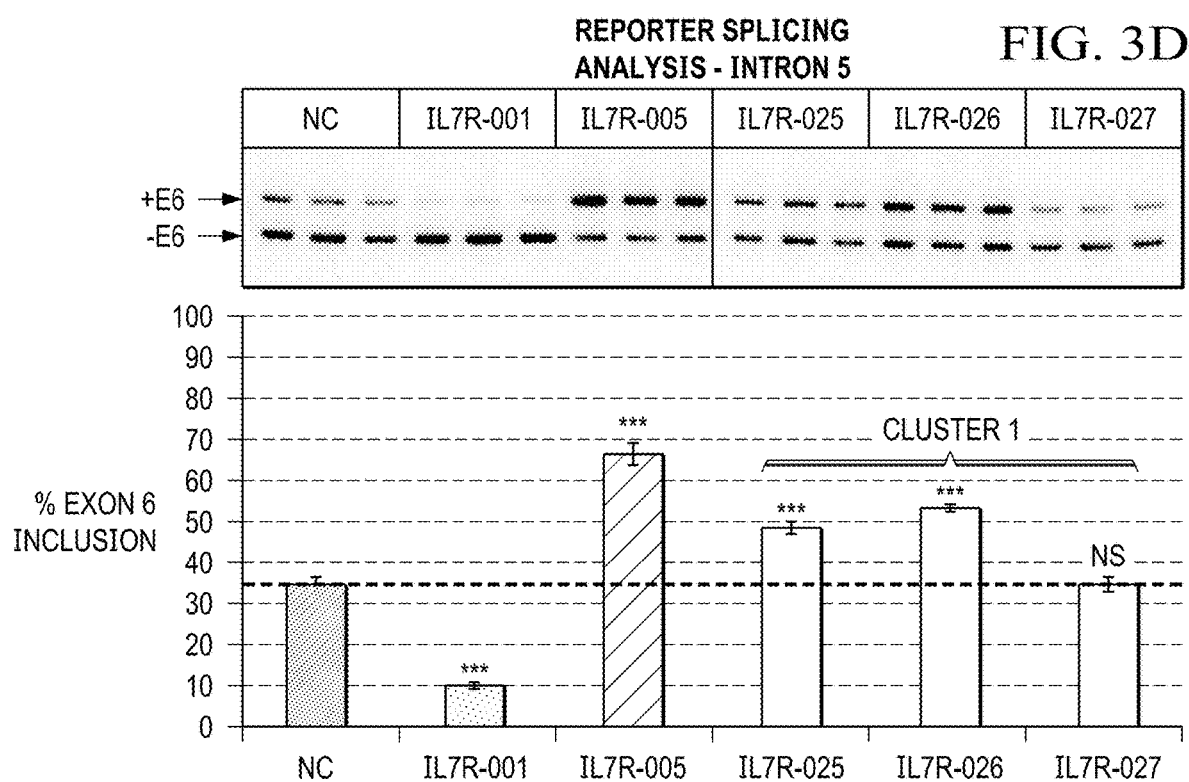

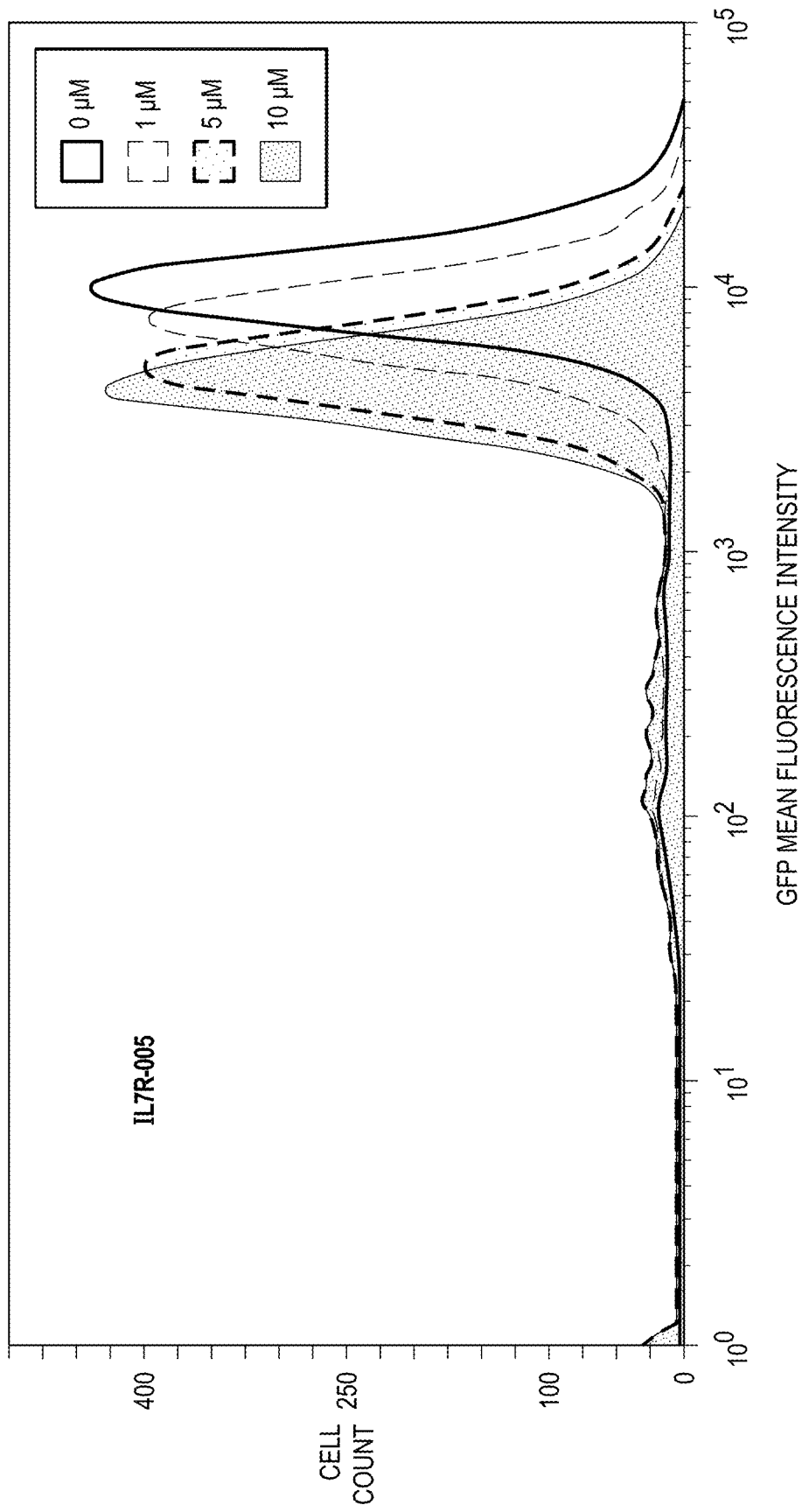

SEQUENCE LISTING

```
<160> NUMBER OF SEQ ID NOS: 50

<210> SEQ ID NO 1
<211> LENGTH: 15
<212> TYPE: RNA
<213> ORGANISM: Artificial Sequence
<220> FEATURE:
<223> OTHER INFORMATION: Synthetic primer

<400> SEQUENCE: 1
gucgcucugu ugguc                                                          15

<210> SEQ ID NO 2
<211> LENGTH: 20
<212> TYPE: RNA
<213> ORGANISM: Artificial Sequence
<220> FEATURE:
<223> OTHER INFORMATION: Synthetic primer

<400> SEQUENCE: 2
uaauaaagag ggugauugug                                                     20

<210> SEQ ID NO 3
<211> LENGTH: 15
<212> TYPE: RNA
<213> ORGANISM: Artificial Sequence
<220> FEATURE:
<223> OTHER INFORMATION: Synthetic primer

<400> SEQUENCE: 3
uuguguggga ucacg                                                          15

<210> SEQ ID NO 4
<211> LENGTH: 15
<212> TYPE: RNA
<213> ORGANISM: Artificial Sequence
<220> FEATURE:
<223> OTHER INFORMATION: Synthetic primer

<400> SEQUENCE: 4
ugggaucacg gacag                                                          15

<210> SEQ ID NO 5
<211> LENGTH: 15
<212> TYPE: RNA
<213> ORGANISM: Artificial Sequence
<220> FEATURE:
<223> OTHER INFORMATION: Synthetic primer

<400> SEQUENCE: 5
ucacggacag ucaga                                                          15
```

```
<210> SEQ ID NO 6
<211> LENGTH: 25
<212> TYPE: RNA
<213> ORGANISM: Artificial Sequence
<220> FEATURE:
<223> OTHER INFORMATION: Synthetic primer

<400> SEQUENCE: 6
uuguguggga ucacggacag ucaga                                              25

<210> SEQ ID NO 7
<211> LENGTH: 18
<212> TYPE: RNA
<213> ORGANISM: Artificial Sequence
<220> FEATURE:
<223> OTHER INFORMATION: Synthetic primer

<400> SEQUENCE: 7
gacagucaga gcuuaagc                                                      18

<210> SEQ ID NO 8
<211> LENGTH: 15
<212> TYPE: RNA
<213> ORGANISM: Artificial Sequence
<220> FEATURE:
<223> OTHER INFORMATION: Synthetic primer

<400> SEQUENCE: 8
ugagaaaacc acaaa                                                         15

<210> SEQ ID NO 9
<211> LENGTH: 15
<212> TYPE: RNA
<213> ORGANISM: Artificial Sequence
<220> FEATURE:
<223> OTHER INFORMATION: Synthetic primer

<400> SEQUENCE: 9 uaccccacu gcaug                                                          15

<210> SEQ ID NO 10
<211> LENGTH: 15
<212> TYPE: RNA
<213> ORGANISM: Artificial Sequence
<220> FEATURE:
<223> OTHER INFORMATION: Synthetic primer

<400> SEQUENCE: 10
gacccuaccc ccacu                                                         15

<210> SEQ ID NO 11
<211> LENGTH: 15
<212> TYPE: RNA
<213> ORGANISM: Artificial Sequence
<220> FEATURE:
<223> OTHER INFORMATION: Synthetic primer

<400> SEQUENCE: 11
ccugagaccc uaccc                                                         15

<210> SEQ ID NO 12
<211> LENGTH: 15
<212> TYPE: RNA
<213> ORGANISM: Artificial Sequence
<220> FEATURE:
```

```
<223> OTHER INFORMATION: Synthetic primer

<400> SEQUENCE: 12
agcacccuga gaccc                                                      15

<210> SEQ ID NO 13
<211> LENGTH: 25
<212> TYPE: RNA
<213> ORGANISM: Artificial Sequence
<220> FEATURE:
<223> OTHER INFORMATION: Synthetic primer

<400> SEQUENCE: 13
agcacccuga gacccuaccc ccacu                                           25

<210> SEQ ID NO 14
<211> LENGTH: 25
<212> TYPE: RNA
<213> ORGANISM: Artificial Sequence
<220> FEATURE:
<223> OTHER INFORMATION: Synthetic primer

<400> SEQUENCE: 14
aggugaccuu cuucaacuaa uaaag                                           25

<210> SEQ ID NO 15
<211> LENGTH: 15
<212> TYPE: RNA
<213> ORGANISM: Artificial Sequence
<220> FEATURE:
<223> OTHER INFORMATION: Synthetic primer

<400> SEQUENCE: 15
caucagcauu uugag                                                      15

<210> SEQ ID NO 16
<211> LENGTH: 25
<212> TYPE: RNA
<213> ORGANISM: Artificial Sequence
<220> FEATURE:
<223> OTHER INFORMATION: Synthetic primer

<400> SEQUENCE: 16
uuuuuucucu gucgcucugu ugguc                                           25

<210> SEQ ID NO 17
<211> LENGTH: 15
<212> TYPE: RNA
<213> ORGANISM: Artificial Sequence
<220> FEATURE:
<223> OTHER INFORMATION: Synthetic primer

<400> SEQUENCE: 17
ucucugucgc ucugu                                                      15

<210> SEQ ID NO 18
<211> LENGTH: 15
<212> TYPE: RNA
<213> ORGANISM: Artificial Sequence
<220> FEATURE:
<223> OTHER INFORMATION: Synthetic primer

<400> SEQUENCE: 18
ggugauugug uggga                                                      15
```

```
<210> SEQ ID NO 19
<211> LENGTH: 22
<212> TYPE: RNA
<213> ORGANISM: Artificial Sequence
<220> FEATURE:
<223> OTHER INFORMATION: Synthetic primer

<400> SEQUENCE: 19
gcuuaagccc cauuuauuga ug                                              22

<210> SEQ ID NO 20
<211> LENGTH: 21
<212> TYPE: RNA
<213> ORGANISM: Artificial Sequence
<220> FEATURE:
<223> OTHER INFORMATION: Synthetic primer

<400> SEQUENCE: 20
cauuuauuga ugagaaaacc a                                               21

<210> SEQ ID NO 21
<211> LENGTH: 15
<212> TYPE: RNA
<213> ORGANISM: Artificial Sequence
<220> FEATURE:
<223> OTHER INFORMATION: Synthetic primer

<400> SEQUENCE: 21
aaaccacaaa gggga                                                      15

<210> SEQ ID NO 22
<211> LENGTH: 16
<212> TYPE: RNA
<213> ORGANISM: Artificial Sequence
<220> FEATURE:
<223> OTHER INFORMATION: Synthetic primer

<400> SEQUENCE: 22
acaaagggga uuaagg                                                     16

<210> SEQ ID NO 23
<211> LENGTH: 18
<212> TYPE: RNA
<213> ORGANISM: Artificial Sequence
<220> FEATURE:
<223> OTHER INFORMATION: Synthetic primer

<400> SEQUENCE: 23
ggggauuaag gcauuuca                                                   18

<210> SEQ ID NO 24
<211> LENGTH: 16
<212> TYPE: RNA
<213> ORGANISM: Artificial Sequence
<220> FEATURE:
<223> OTHER INFORMATION: Synthetic primer

<400> SEQUENCE: 24
uuaaggcauu ucacga                                                     16

<210> SEQ ID NO 25
<211> LENGTH: 16
<212> TYPE: RNA
<213> ORGANISM: Artificial Sequence
<220> FEATURE:
<223> OTHER INFORMATION: Synthetic primer
```

<400> SEQUENCE: 25
ucacgaauuu agugcc					16

<210> SEQ ID NO 26
<211> LENGTH: 18
<212> TYPE: RNA
<213> ORGANISM: Artificial Sequence
<220> FEATURE:
<223> OTHER INFORMATION: Synthetic primer

<400> SEQUENCE: 26
cccacauuac uaaguaaa					18

<210> SEQ ID NO 27
<211> LENGTH: 15
<212> TYPE: RNA
<213> ORGANISM: Artificial Sequence
<220> FEATURE:
<223> OTHER INFORMATION: Synthetic primer

<400> SEQUENCE: 27
ggcccacauu acuaa					15

<210> SEQ ID NO 28
<211> LENGTH: 15
<212> TYPE: RNA
<213> ORGANISM: Artificial Sequence
<220> FEATURE:
<223> OTHER INFORMATION: Synthetic primer

<400> SEQUENCE: 28
aagugggccc acauu					15

<210> SEQ ID NO 29
<211> LENGTH: 15
<212> TYPE: RNA
<213> ORGANISM: Artificial Sequence
<220> FEATURE:
<223> OTHER INFORMATION: Synthetic primer

<400> SEQUENCE: 29
auaauaagug ggccc					15

<210> SEQ ID NO 30
<211> LENGTH: 19
<212> TYPE: RNA
<213> ORGANISM: Artificial Sequence
<220> FEATURE:
<223> OTHER INFORMATION: Synthetic primer

<400> SEQUENCE: 30
ucucuuaacu gaaaagcaa					19

<210> SEQ ID NO 31
<211> LENGTH: 22
<212> TYPE: RNA
<213> ORGANISM: Artificial Sequence
<220> FEATURE:
<223> OTHER INFORMATION: Synthetic primer

<400> SEQUENCE: 31
caaauauguc ucuuaacuga aa					22

<210> SEQ ID NO 32
<211> LENGTH: 20

```
<212> TYPE: RNA
<213> ORGANISM: Artificial Sequence
<220> FEATURE:
<223> OTHER INFORMATION: Synthetic primer

<400> SEQUENCE: 32
ugucaaauau gucucuuaac                                               20

<210> SEQ ID NO 33
<211> LENGTH: 17
<212> TYPE: RNA
<213> ORGANISM: Artificial Sequence
<220> FEATURE:
<223> OTHER INFORMATION: Synthetic primer

<400> SEQUENCE: 33
gcugucaaau augcuc                                                   17

<210> SEQ ID NO 34
<211> LENGTH: 17
<212> TYPE: RNA
<213> ORGANISM: Artificial Sequence
<220> FEATURE:
<223> OTHER INFORMATION: Synthetic primer

<400> SEQUENCE: 34
auaaagcugu caaauau                                                  17

<210> SEQ ID NO 35
<211> LENGTH: 15
<212> TYPE: RNA
<213> ORGANISM: Artificial Sequence
<220> FEATURE:
<223> OTHER INFORMATION: Synthetic primer

<400> SEQUENCE: 35
uccauaaagc uguca                                                    15

<210> SEQ ID NO 36
<211> LENGTH: 15
<212> TYPE: RNA
<213> ORGANISM: Artificial Sequence
<220> FEATURE:
<223> OTHER INFORMATION: Synthetic primer

<400> SEQUENCE: 36
aucccuccau aaagc                                                    15

<210> SEQ ID NO 37
<211> LENGTH: 17
<212> TYPE: RNA
<213> ORGANISM: Artificial Sequence
<220> FEATURE:
<223> OTHER INFORMATION: Synthetic primer

<400> SEQUENCE: 37
aaccaaaauc ccuccau                                                  17

<210> SEQ ID NO 38
<211> LENGTH: 21
<212> TYPE: RNA
<213> ORGANISM: Artificial Sequence
<220> FEATURE:
<223> OTHER INFORMATION: Synthetic primer

<400> SEQUENCE: 38
```

-continued ugccuuuuaa accaaaaucc c                    21

<210> SEQ ID NO 39
<211> LENGTH: 21
<212> TYPE: RNA
<213> ORGANISM: Artificial Sequence
<220> FEATURE:
<223> OTHER INFORMATION: Synthetic primer

<400> SEQUENCE: 39
gucaaugccu uuuaaaccaa a                    21

<210> SEQ ID NO 40
<211> LENGTH: 21
<212> TYPE: RNA
<213> ORGANISM: Artificial Sequence
<220> FEATURE:
<223> OTHER INFORMATION: Synthetic primer

<400> SEQUENCE: 40
cccaagucaa ugccuuuuaa a                    21

<210> SEQ ID NO 41
<211> LENGTH: 15
<212> TYPE: RNA
<213> ORGANISM: Artificial Sequence
<220> FEATURE:
<223> OTHER INFORMATION: Synthetic primer

<400> SEQUENCE: 41
gucacccaag ucaau                    15

<210> SEQ ID NO 42
<211> LENGTH: 15
<212> TYPE: RNA
<213> ORGANISM: Artificial Sequence
<220> FEATURE:
<223> OTHER INFORMATION: Synthetic primer

<400> SEQUENCE: 42
gccuggucac ccaag                    15

<210> SEQ ID NO 43
<211> LENGTH: 15
<212> TYPE: RNA
<213> ORGANISM: Artificial Sequence
<220> FEATURE:
<223> OTHER INFORMATION: Synthetic primer

<400> SEQUENCE: 43
aauuuagugc ccagu                    15

<210> SEQ ID NO 44
<211> LENGTH: 15
<212> TYPE: RNA
<213> ORGANISM: Artificial Sequence
<220> FEATURE:
<223> OTHER INFORMATION: Synthetic primer

<400> SEQUENCE: 44
agugcccagu auccc                    15

<210> SEQ ID NO 45
<211> LENGTH: 15
<212> TYPE: RNA
<213> ORGANISM: Artificial Sequence

```
<220> FEATURE:
<223> OTHER INFORMATION: Synthetic primer

<400> SEQUENCE: 45
ccaguauccc uaucu                                                    15

<210> SEQ ID NO 46
<211> LENGTH: 17
<212> TYPE: RNA
<213> ORGANISM: Artificial Sequence
<220> FEATURE:
<223> OTHER INFORMATION: Synthetic primer

<400> SEQUENCE: 46
aucccuaucu auccuca                                                  17

<210> SEQ ID NO 47
<211> LENGTH: 15
<212> TYPE: RNA
<213> ORGANISM: Artificial Sequence
<220> FEATURE:
<223> OTHER INFORMATION: Synthetic primer

<400> SEQUENCE: 47
uaucuauccu cagcg                                                    15

<210> SEQ ID NO 48
<211> LENGTH: 16
<212> TYPE: RNA
<213> ORGANISM: Artificial Sequence
<220> FEATURE:
<223> OTHER INFORMATION: Synthetic primer

<400> SEQUENCE: 48
auccucagcg aauuuc                                                   16

<210> SEQ ID NO 49
<211> LENGTH: 15
<212> TYPE: RNA
<213> ORGANISM: Artificial Sequence
<220> FEATURE:
<223> OTHER INFORMATION: Synthetic primer

<400> SEQUENCE: 49
cagcgaauuu ccaca                                                    15

<210> SEQ ID NO 50
<211> LENGTH: 24
<212> TYPE: RNA
<213> ORGANISM: Artificial Sequence
<220> FEATURE:
<223> OTHER INFORMATION: Synthetic primer

<400> SEQUENCE: 50 aauuccaca guuaauuuca uaag                                           24
```

SOLUBLE INTERLEUKIN-7 RECEPTOR (SIL7R) MODULATING THERAPY TO TREAT AUTOIMMUNE DISEASES AND CANCER

CROSS-REFERENCE TO RELATED APPLICATIONS

This application claims priority to U.S. Ser. No. 17/027,467, filed on Sep. 21, 2020, PCT/US2019/023719, filed Mar. 22, 2019, and U.S. Provisional Application Ser. No. 62/646,716, filed Mar. 22, 2018, the entire contents of each is incorporated herein by reference.

STATEMENT OF FEDERALLY FUNDED RESEARCH

This invention was made with government support under F32-NS087899 awarded by NIH. The government has certain rights in the invention.

TECHNICAL FIELD OF THE INVENTION

The present invention relates in general to the field of novel therapies that reduce or increase soluble IL7R (sIL7R) to treat autoimmune diseases (e.g., multiple sclerosis) or cancer, respectively.

BACKGROUND OF THE INVENTION

Without limiting the scope of the invention, its background is described in connection with multiple sclerosis, as an example.

Multiple Sclerosis (MS) is a chronic autoimmune disease characterized by self-reactive immune cell-mediated damage to neuronal myelin sheaths in the central nervous system (CNS) that leads to axonal demyelination, neuronal death and progressive neurological dysfunction. Up to date, there is no cure for the disease and available treatments can only slow down disease progression, often by globally suppressing the immune system, causing a plethora of adverse side effects that could be severe or lethal. This global immunosuppression is the major limitation of current therapies.

The breach of immunological tolerance that leads to MS is thought to originate from complex interactions between environmental and genetic factors. Under this view, the genetic background of an individual could generate an environment permissive for the survival of self-reactive lymphocytes, which could be subsequently activated by the presence of an environmental trigger, usually in the form of viral or bacterial infection.

The present inventors and others have previously shown that the variant rs6897932 (C/T, where C is the risk allele) within exon 6 of the Interleukin-7 receptor (IL7R) gene is strongly associated with increased MS risk (Gregory et al., 2007; International Multiple Sclerosis Genetics et al., 2007; Lundmark et al., 2007). Furthermore, the present inventors showed that the risk 'C' allele of this variant increases skipping of the exon (Evsyukova et al., 2013; Gregory et al., 2007), leading to up-regulation of sIL7R (Hoe et al., 2010; Lundstrom et al., 2013). Importantly, sIL7R has been shown to exacerbate the clinical progression and severity of the disease in the Experimental Autoimmune Encephalomyelitis (EAE) mouse model of MS, presumably by potentiating the bioavailability and/or bioactivity of IL7 cytokine (Lundstrom et al., 2013). Further supporting a role of sIL7R in the pathogenesis of multiple sclerosis, and perhaps autoimmunity in general, elevated levels of sIL7R protein or RNA have been reported in patients of multiple sclerosis (McKay et al. 2008), rheumatoid arthritis (Badot et al., 2011), type 1 diabetes (Monti et al., 2013), and systemic lupus erythematosus (Lauwerys et al., 2014). Collectively, these data link elevated levels of sIL7R to the pathogenesis of MS and autoimmunity, and position alternative splicing of IL7R exon 6 as a novel therapeutic target for MS and autoimmunity.

While these references teach that the presence of sIL7R correlates with multiple sclerosis, and animal studies demonstrate that sIL7R exacerbates an MS-like condition, a need remains for novel composition and methods for treating autoimmune diseases, such as MS, by targeting the production of sIL7R.

Many different etiologies exist for autoimmune diseases, and each of these can be the target of accurate or personalized therapies. In this invention, the present inventors address one such etiology caused by elevated levels of sIL7R, which is likely to affect as many as 60% of MS patients and a significant number of patients with other autoimmune disorders caused by elevated sIL7R.

Immuno-oncology is a rapidly growing field that holds great promise for patients with heretofore intractable cancers; however, the impact of immunotherapy has been limited by very low response rates in some cancers and individuals.

Antisense oligonucleotide therapy targets a genetic sequence of a particular gene that is causative of a particular disease with a short oligonucleotide that is complementary to a target sequence. Typically, a strand of nucleic acids is designed (DNA, RNA or a chemical analogue) that binds to the messenger RNA (mRNA) or pre-mRNA of the target sequence. In the case of splice-modulating antisense oligonucleotides (SM-ASOs), the complementary nucleic acid is designed to bind a specific sequence in a pre-mRNA that modifies the exon content of the resulting mRNA. Antisense oligonucleotides have been used to target diseases such as cancers, diabetes, amyotrophic lateral sclerosis (ALS), Duchenne muscular dystrophy, spinal muscular atrophy, Ataxia-telangiectasia, asthma, and arthritis. Several antisense oligonucleotide drugs have been approved by the U.S. Food and Drug Administration (FDA), for the treatment for cytomegalovirus retinitis, homozygous familial hypercholesterolemia, Duchenne muscular dystrophy, and spinal muscular atrophy, to name a few, with the latter two been SM-ASOs. However, in each case the oligonucleotide target sequence must be tailored to the specific etiology underlying the disease in question.

SUMMARY OF THE INVENTION

In one embodiment, the present invention includes a method of treating a disease or condition with elevated levels of a soluble isoform of Interleukin 7 receptor (sIL7R) in a subject in need thereof, the method comprising: administering an effective amount of a composition comprising an oligonucleotide that specifically binds to a sequence of the Interleukin-7 receptor (IL7R) pre-mRNA that influences splicing of exon 6, wherein the oligonucleotide increases inclusion of exon 6 in IL7R pre-mRNAs and decreases expression of the soluble isoform of IL7R (sIL7R). In one aspect, the oligonucleotide is an antisense oligonucleotide (ASO) or a splice-modulating antisense oligonucleotide (SM-ASO). In another aspect, the oligonucleotide in the composition specifically binds to a sequence in IL7R pre-mRNA in at least one of the group consisting of an exonic splicing silencer (ESS) and/or an intronic splicing silencer (ISS), thereby enhancing inclusion of exon 6 in IL7R pre-mRNAs, and reducing expression of sIL7R. In another aspect, the oligonucleotide in the composition specifically binds to a sequence on IL7R pre-mRNA at intron-exon splice sites, branchpoint sequences, and/or polypyrimidine tracts. In another aspect, at least one or more nucleotide(s) in the oligonucleotide contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and combinations of two or more of any of the foregoing. In another aspect, at least one or more nucleotide(s) in the oligonucleotide contains a non-naturally occurring modification to the nucleotide bases. In another aspect, the oligonucleotide is selected from any of the SEQ IDs in Table 1 (SEQ ID NOS:1-13), or portions thereof, either alone or in combination, or a sequence having at least 70, 75, 80, 84, 85, 88, 92, 93, 94, 95, or 96% identity over the full target sequences within IL7R RNAs. In another aspect, the oligonucleotide targets any of the SEQ IDs in Table 1 (SEQ ID NOS:1-13), either fully or partially. In another aspect, the composition further comprises a pharmaceutically acceptable excipient, salts, or carrier. In another aspect, the disease or condition is an autoimmune disorder is selected from at least one of the following: multiple sclerosis, type I diabetes, rheumatoid arthritis, systemic lupus erythematosus, atopic dermatitis, ankylosing spondylitis, primary biliary cirrhosis, or inflammatory bowel syndromes such as ulcerative colitis, crohn's disease or any other conditions where sIL7R is elevated when compared to a normal subject without a disease or condition. In another aspect, the disease or condition is an inflammatory disease or condition. In another aspect, the oligonucleotide enhances the degradation of IL7R mRNAs that lack exon 6 by targeting an IL7R exon 5-exon 7 boundary, e.g., with ASOs, siRNAs, shRNAs that decrease stability of sIL7R RNA (e.g., increase degradation), and/or ASOs that decrease translation of sIL7R RNA. In another aspect, the method further comprises a combination therapy of the SM-ASO and one or more active agents effective for treating autoimmune diseases such as, but not limited to, mitoxatrone, interferon beta-1a, PEG-interferon beta-1a, azathioprine, fingolimod, natalizumab, methylprednisolone, or ocrelizumab. In another aspect, the method further comprises steps of obtaining cells from the patient and modifying the cells to transiently or permanently express the oligonucleotide that specifically binds to a sequence of the Interleukin-7 receptor (IL7R) pre-mRNA that influences splicing of exon 6. In another aspect, the method further comprises generating a vector that expresses the oligonucleotide that specifically binds to a sequence of the Interleukin-7 receptor (IL7R) pre-mRNA that influences splicing of exon 6 for use in gene therapy, and treating the patient with the vector.

In another embodiment, the present invention includes a composition comprising an oligonucleotide that is an antisense oligonucleotide (ASO) or a splice-modulating antisense oligonucleotide (SM-ASO), that specifically binds to a sequence in pre-mRNAs of Interleukin 7 receptor (IL7R) that influences splicing of exon 6, wherein the SM-ASO increases inclusion of exon 6 in IL7R pre-mRNAs and decreases expression of the soluble isoform of IL7R (sIL7R). In one aspect, the oligonucleotide in the composition specifically binds to a sequence in IL7R pre-mRNA in at least one of the group consisting of an exonic splicing silencer (ESS) and/or an intronic splicing silencer (ISS), thereby enhancing inclusion of exon 6 in IL7R pre-mRNAs, and reducing expression of sIL7R. In another aspect, the oligonucleotide in the composition specifically binds to a sequence on IL7R pre-mRNA at intron-exon splice sites, branchpoint sequences, and/or polypyrimidine tracts. In another aspect, at least one or more nucleotide(s) in the oligonucleotide contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and any combinations of two or more of any of the foregoing. In another aspect, at least one or more nucleotide(s) in the oligonucleotide contains a non-naturally occurring modification to the nucleotide bases. In another aspect, the oligonucleotide is selected from any of the SEQ IDs in Table 1 (SEQ ID NOS:1-13), or portions thereof, either alone or in combination, or a sequence having at least 70, 75, 80, 84, 85, 88, 92, 93, 94, 95, or 96% identity over the full target sequence within IL7R RNAs. In another aspect, the oligonucleotide targets any of the SEQ IDs in Table 1 (SEQ ID NOS:1-13), either fully or partially. In another aspect, the composition further comprises a pharmaceutically acceptable excipient, salts, or carrier. In another aspect, the composition is adapted for administration to treat an autoimmune disorder selected from at least one of the following: multiple sclerosis, type I diabetes, rheumatoid arthritis, systemic lupus erythematosus, atopic dermatitis, ankylosing spondylitis, primary biliary cirrhosis, inflammatory bowel syndromes such as ulcerative colitis and crohn's disease, or any other conditions where sIL7R is elevated. In another aspect, the oligonucleotide enhances the degradation of IL7R mRNAs that lack exon 6 by targeting an IL7R exon 5-exon 7 boundary, e.g., with ASOs, siRNAs, shRNAs that decrease stability of sIL7R RNA (e.g., increase degradation), and/or ASOs that decrease translation of sIL7R RNA.

In yet another embodiment, the present invention includes a method of increasing inclusion of exon 6 of an Interleukin-7 receptor (IL7R) pre-mRNA, the method comprising: contacting a splice modulating antisense oligonucleotide (SM-ASO) that specifically binds to a sequence of the Interleukin-7 receptor (IL7R) pre-mRNA that influences splicing of exon 6, wherein the SM-ASO increases inclusion of exon 6 in IL7R pre-mRNAs and decreases expression of the soluble isoform of IL7R (sIL7R). In one aspect, the SM-ASO in the composition specifically binds to a sequence in IL7R pre-mRNA in at least one of the group consisting of an exonic splicing silencer (ESS) and/or an intronic splicing silencer (ISS), thereby enhancing inclusion of exon 6 in IL7R pre-mRNAs, and reducing expression of sIL7R. In another aspect, the SM-ASO in the composition specifically binds to a sequence on IL7R pre-mRNA at intron-exon splice sites, branchpoint sequences, and/or polypyrimidine tracts. In another aspect, at least one or more nucleotide(s) in the SM-ASO contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and any combinations of two or more of any of the foregoing. In another aspect, at least one or more nucleotide(s) in the SM-ASO contains a non-naturally occurring modification to the nucleotide bases. In another aspect, the SM-ASO enhances the degradation of IL7R mRNAs that lack exon 6 by targeting an IL7R exon 5-exon 7 boundary, e.g., with ASOs, siRNAs, shRNAs that decrease stability of sIL7R RNA (e.g., increase degradation), and/or ASOs that decrease translation of sIL7R RNA. In another aspect, the SM-ASO blocks the translation of IL7R mRNAs that lack exon 6. In another aspect, the SM-ASO is selected from any of the SEQ IDs in Table 1 (SEQ ID NOS:1-13), or portions thereof either alone or in combination, or a sequence having at least 70, 75, 80, 84, 85, 88, 92, 93, 94, 95, or 96% identity over the full target sequence within IL7R RNAs. In another aspect, the oligonucleotide targets any of the SEQ IDs in Table 1 (SEQ ID NOS:1-13), either fully or partially. In another aspect, the composition further comprises a pharmaceutically acceptable excipient, salts, or carrier. In another aspect, the autoimmune disorder is selected from at least one of the following: multiple sclerosis, type I diabetes, rheumatoid arthritis, systemic lupus erythematosus, atopic dermatitis, ankylosing spondylitis, primary biliary cirrhosis, inflammatory bowel syndromes such as ulcerative colitis and crohn's disease, or any conditions where sIL7R is elevated. In another aspect, the method further comprises steps of obtaining cells from the patient and modifying the cells to transiently or permanently express the oligonucleotide that specifically binds to a sequence of the Interleukin-7 receptor (IL7R) pre-mRNA that influences splicing of exon 6. In another aspect, the method further comprises generating a vector that expresses the oligonucleotide that specifically binds to a sequence of the Interleukin-7 receptor (IL7R) pre-mRNA that influences splicing of exon 6 for use in gene therapy, and treating the patient with the vector.

In another embodiment, the present invention includes a composition for increasing inclusion of exon 6 in an Interleukin-7 receptor (IL7R) pre-mRNA, the method comprising: contacting a splice modulating antisense oligonucleotide (SM-ASO) that specifically binds to a sequence in the Interleukin-7 receptor (IL7R) pre-mRNA that influences splicing of exon 6, wherein the SM-ASO increases inclusion of exon 6 in IL7R pre-mRNAs and decreases expression of the soluble isoform of IL7R (sIL7R). In one aspect, the composition further comprises a combination therapy of the SM-ASO with one or more active agents effective for treating autoimmune diseases selected from, but not limited to, mitoxatrone, interferon beta-1a, PEG-interferon beta-1a, azathioprine, fingolimod, natalizumab, methylprednisolone, or ocrelizumab.

In another embodiment, the present invention includes a vector that expresses a nucleic acid comprising an oligonucleotide that is an antisense oligonucleotide (ASO), or a splice-modulating antisense oligonucleotide (SM-ASO), that specifically binds to a sequence in the Interleukin-7 receptor (IL7R) pre-mRNA that influences splicing of exon 6, wherein the SM-ASO increases inclusion of exon 6 in IL7R pre-mRNAs and decreases expression of the soluble isoform of IL7R (sIL7R). In one aspect, the vector is a viral vector or a plasmid.

In another embodiment, the present invention includes a vector that expresses a nucleic acid comprising an antisense oligonucleotide (ASO), splice-modulating antisense oligonucleotide (SM-ASO), translation-blocking antisense oligonucleotide, siRNA, shRNA or miRNA, that specifically binds a sequence in the Interleukin-7 receptor (IL7R) pre-mRNA that enhances inhibition or degradation of IL7R RNAs lacking exon 6, wherein the nucleic acid decreases expression of the soluble isoform of IL7R (sIL7R). In one aspect, the vector is a viral vector or a plasmid.

In another embodiment, the present invention includes a method of treating multiple sclerosis in a subject in need thereof, the method comprising: administering an effective amount of a composition comprising a splice modulating antisense oligonucleotide (SM-ASO) that specifically binds a sequence of an Interleukin-7 receptor (IL7R) pre-mRNA that influences splicing of exon 6, wherein the SM-ASO increases inclusion of exon 6 in IL7R pre-mRNAs and decreases expression of the soluble isoform of IL7R (sIL7R) in a pharmaceutically acceptable excipient. In one aspect, the method further comprises a combination therapy of the SM-ASO and one or more active agents effective for treating multiple sclerosis disease. In another aspect, the one or more agents for treating multiple sclerosis are selected from, but not limited to, mitoxatrone, interferon beta-1a, PEG-interferon beta-1a, azathioprine, fingolimod, natalizumab, methylprednisolone, or ocrelizumab.

In another embodiment, the present invention includes a method of treating a cancer in a subject in need thereof, the method comprising: administering an effective amount of a composition comprising an oligonucleotide that specifically binds a sequence of the Interleukin-7 receptor (IL7R) pre-mRNA that influences splicing of exon 6, wherein the oligonucleotide decreases inclusion of exon 6 in IL7R pre-mRNAs and increases expression of the soluble isoform of IL7R (sIL7R). In one aspect, the oligonucleotide is an antisense oligonucleotide (ASO) or a splice-modulating antisense oligonucleotide (SM-ASO). In another aspect, the oligonucleotide in the composition specifically binds to a sequence in IL7R pre-mRNA in at least one of the group consisting of an exonic splicing enhancer (ESE) and/or an intronic splicing enhancer (ISE), thereby decreasing inclusion of exon 6, and increasing expression of sIL7R. In another aspect, the oligonucleotide in the composition specifically binds to a sequence on IL7R pre-mRNA at intron-exon splice sites, branchpoint sequences, and/or polypyrimidine tracts. In another aspect, at least one or more nucleotide(s) in the oligonucleotide contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and combinations of two or more of any of the foregoing. In another aspect, at least one or more nucleotide(s) in the oligonucleotide contains a non-naturally occurring modification to the nucleotide bases. In another aspect, the oligonucleotide is selected from any of the SEQ IDs in Table 2 (SEQ ID NOS:14-50), or portions thereof, either alone or in combination, or a sequence having at least 70, 75, 80, 84, 85, 88, 92, 93, 94, 95, or 96% identity over the full target sequences within IL7R RNAs. In another aspect, the oligonucleotide targets any of the SEQ IDs in Table 2 (SEQ ID NOS:14-50), or portions thereof. In another aspect, the composition further comprises a pharmaceutically acceptable excipient, salts, or carrier. In another aspect, the cancer demonstrates low response to conventional immunotherapy (e.g., hepatocellular carcinoma). In another aspect, the method further comprises a combination therapy of the SM-ASO and one or more active agents effective for treating cancer such as, but not limited to, immune check point inhibitors (e.g., nivolumab), therapeutic antibodies (e.g., Herceptin), conventional chemotherapy (e.g., taxol), or therapeutic radiation. In another aspect, the method further comprises steps of obtaining cells from the patient and modifying the cells to transiently or permanently express the oligonucleotide that specifically binds to a sequence of the Interleukin-7 receptor (IL7R) pre-mRNA that influences splicing of exon 6. In another aspect, the method further comprises generating a vector that expresses the oligonucleotide that specifically binds to a sequence of the Interleukin-7 receptor (IL7R) pre-mRNA that influences splicing of exon 6 for use in gene therapy, and treating the patient with the vector.

In another embodiment, the present invention includes a composition comprising an oligonucleotide that is an antisense oligonucleotide (ASO) or a splice-modulating antisense oligonucleotide (SM-ASO), that specifically binds to a sequence in interleukin 7 receptor (IL7R) pre-mRNA that influences splicing of exon 6, wherein the SM-ASO decreases inclusion of exon 6 in IL7R pre-mRNAs and increases expression of the soluble isoform of IL7R (sIL7R). In another aspect, the oligonucleotide in the composition specifically binds to a sequence in IL7R pre-mRNA in at least one of the group consisting of an exonic splicing enhancer (ESE) and/or an intronic splicing enhancer (ISE), thereby decreasing inclusion of exon 6, and increasing expression of sIL7R. In another aspect, the oligonucleotide in the composition specifically binds to a sequence on IL7R pre-mRNA at intron-exon splice sites, branchpoint sequences, and/or polypyrimidine tracts. In another aspect, at least one or more nucleotide(s) in the oligonucleotide contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and any combinations of two or more of any of the foregoing. In another aspect, at least one or more nucleotide(s) in the oligonucleotide contains a non-naturally occurring modification to the nucleotide bases. In another aspect, the oligonucleotide is selected from any of the SEQ IDs in Table 2 (SEQ ID NOS:14-50), or portions thereof, either alone or in combination, or a sequence having at least 70, 75, 80, 84, 85, 88, 92, 93, 94, 95, or 96% identity over the full target sequence within IL7R RNAs. In another aspect, the oligonucleotide targets any of the SEQ IDs in Table 2 (SEQ ID NOS:14-50), either fully or partially. In another aspect, the composition further comprises a pharmaceutically acceptable excipient, salts, or carrier. In another aspect, the composition is adapted for administration to treat a cancer.

In yet another embodiment, the present invention includes a method of decreasing inclusion of exon 6 in Interleukin-7 receptor (IL7R) pre-mRNA, the method comprising: contacting a splice modulating antisense oligonucleotide (SM-ASO) that specifically binds to a sequence of the Interleukin-7 receptor (IL7R) pre-mRNA that influences splicing of exon 6, wherein the SM-ASO decreases inclusion of exon 6 in IL7R pre-mRNAs and increases expression of the soluble isoform of IL7R (sIL7R). In another aspect, the oligonucleotide in the composition specifically binds to a sequence in IL7R pre-mRNA in at least one of the group consisting of an exonic splicing enhancer (ESE) and/or an intronic splicing enhancer (ISE), thereby decreasing inclusion of exon 6, and increasing expression of sIL7R. In another aspect, the SM-ASO in the composition specifically binds to a sequence on IL7R pre-mRNA at intron-exon splice sites, branchpoint sequences, and/or polypyrimidine tracts. In another aspect, at least one or more nucleotide(s) in the SM-ASO contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and any combinations of two or more of any of the foregoing. In another aspect, at least one or more nucleotide(s) in the SM-ASO contains a non-naturally occurring modification to the nucleotide bases. In another aspect, the SM-ASO enhances the stability of IL7R mRNAs that lack exon 6 by targeting an IL7R exon 5-exon 7 boundary. In another aspect, the SM-ASO enhances the translation of IL7R mRNAs that lack exon 6. In another aspect, the SM-ASO is selected from any of the SEQ IDs in Table 2, or portions thereof, either alone or in combination, or a sequence having at least 70, 75, 80, 84, 85, 88, 92, 93, 94, 95, or 96% identity over the full target sequence within IL7R RNAs. In another aspect, the oligonucleotide targets any of the SEQ IDs in Table 2, either fully or partially. In another aspect, the composition further comprises a pharmaceutically acceptable excipient, salts, or carrier. In another aspect, the disorder is a type of cancer. In another aspect, the method further comprises steps of obtaining cells from the patient and modifying the cells to transiently or permanently express the oligonucleotide that specifically binds to a sequence of the Interleukin-7 receptor (IL7R) pre-mRNA that influences splicing of exon 6. In another aspect, the method further comprises generating a vector that expresses the oligonucleotide that specifically binds to a sequence of the Interleukin-7 receptor (IL7R) pre-mRNA that influences splicing of exon 6 for use in gene therapy, and treating the patient with the vector.

In another embodiment, the present invention includes a composition for increasing inclusion of exon 6 in an Interleukin-7 receptor (IL7R) pre-mRNA, the method comprising: contacting a splice modulating antisense oligonucleotide (SM-ASO) that specifically binds to a sequence in the Interleukin-7 receptor (IL7R) pre-mRNA that influences splicing of exon 6, wherein the SM-ASO decreases inclusion of exon 6 in IL7R pre-mRNAs and increases expression of the soluble isoform of IL7R (sIL7R). In one aspect, the composition further comprises a combination therapy of the SM-ASO with one or more active agents effective for treating cancer, such as, but not limited to, immune check point inhibitors (e.g., nivolumab), therapeutic antibodies (e.g., Herceptin), conventional chemotherapy (e.g., taxol), or therapeutic radiation.

In another embodiment, the present invention includes a vector that expresses a nucleic acid comprising an oligonucleotide that is an antisense oligonucleotide (ASO), or a splice-modulating antisense oligonucleotide (SM-ASO), that specifically binds a sequence in the Interleukin-7 receptor (IL7R) pre-mRNA that influences splicing of exon 6, wherein the SM-ASO decreases inclusion of exon 6 in IL7R pre-mRNAs and increases expression of the soluble isoform of IL7R (sIL7R). In one aspect, the vector is a viral vector or a plasmid.

BRIEF DESCRIPTION OF THE DRAWINGS

For a more complete understanding of the features and advantages of the present invention, reference is now made to the detailed description of the invention along with the accompanying figures and in which:

FIGS. 3A to 3E show an SM-ASO walk screen targeting sequences in IL7R introns 5 and 6.

FIGS. 5A to 5D show the dose-response effects of lead SM-ASOs that reduce sIL7R on modulation of IL7R exon 6 splicing.

DETAILED DESCRIPTION OF THE INVENTION

Figure 1A:
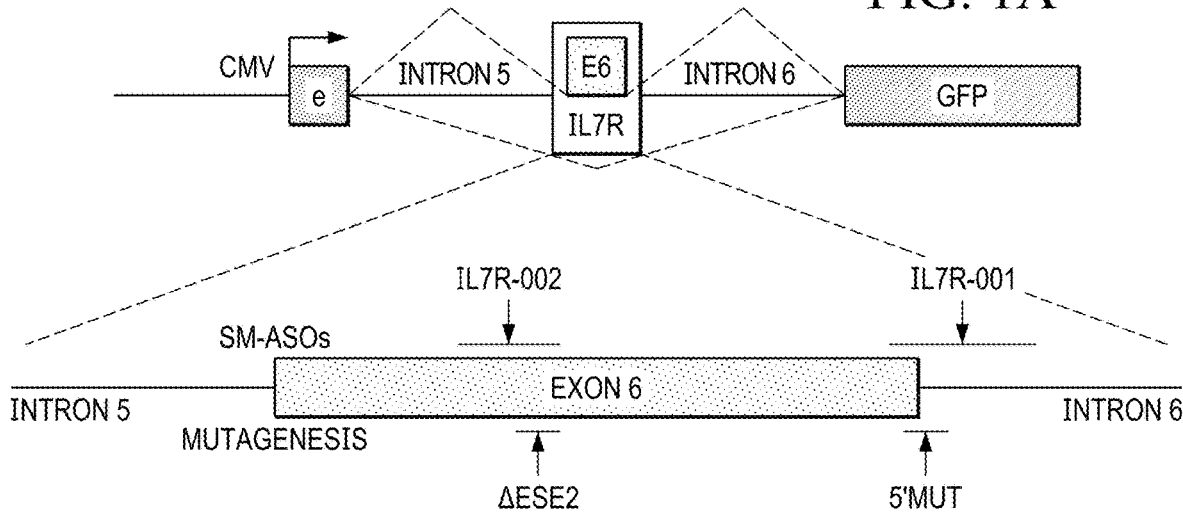
FIGS. 1A to 1C show validation of a GFP-IL7R fluorescent splicing reporter for screening of splice-modulating antisense oligonucleotides (SM-ASOs).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention is directed to novel compositions and methods that reduce or increase soluble IL7R (sIL7R) to treat autoimmune diseases (e.g., multiple sclerosis) or cancer, respectively. The present invention uses SM-ASOs to control alternative splicing of the Interleukin 7 receptor (IL7R) pre-mRNAs, either to prevent or diminish expression of sIL7R or the opposite to increase expression of sIL7R. For example, given the ability of sIL7R to enhance self-reactivity it is demonstrated herein that increasing sIL7R levels enhances response to currently employed immunotherapies (e.g., immune check point inhibitors).

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, organic synthesis, nucleic acid chemistry and nucleic acid hybridization are those well known and commonly employed in the art. Further, standard techniques can be used for nucleic acid and peptide synthesis. Such techniques and procedures are generally performed according to conventional methods known in the art and from various general references (e.g., Sambrook and Russell, 2012, Molecular Cloning, A Laboratory Approach, Cold Spring Harbor Press, Cold Spring Harbor, N.Y., and Ausubel et al., 2012, Current Protocols in Molecular Biology, John Wiley & Sons, NY), relevant portions incorporated herein by reference.

Conventional notations are used herein to describe polynucleotide sequences, e.g., the left-hand end of a single-stranded polynucleotide sequence is the 5'-end and vice versa for the 3'-end (right-hand end); the left-hand direction of a double-stranded polynucleotide sequence is referred to as the 5'-direction and vice versa for the 3'-direction (right-hand direction), with regard to sequences, such as those that become coding sequences. The direction of 5' to 3' addition of nucleotides to nascent RNA transcripts is referred to as the transcription direction. The DNA strand having the same sequence as an mRNA is referred to as the "coding strand". Sequences on the DNA or RNA strand that are located 5' to a reference point on the DNA or RNA are referred to as "upstream sequences", and sequences on the DNA or RNA strand that are 3' to a reference point on the DNA or RNA are referred to as "downstream sequences."

As used herein, the term "antisense" refers to an oligonucleotide having a sequence that hybridizes to a target sequence in RNA by Watson-Crick base pairing, to form an RNA:oligonucleotide heteroduplex with the target sequence, typically with an mRNA or pre-mRNA. The antisense oligonucleotide may have exact sequence complementarity to the target sequence or near complementarity. These antisense oligonucleotides may block or inhibit translation of the mRNA, modify the processing of an mRNA to produce a splice variant of the mRNA, and/or promote specific degradation of a given mRNA or variant of an mRNA. One non-limiting example can also be RNase H dependent degradation. It is not necessary that the antisense sequence be complementary solely to the coding portion of the RNA molecule. The antisense sequence may be complementary to regulatory sequences specified on the non-coding region of an RNA molecule (e.g. introns, untranslated regions) encoding a protein, which regulatory sequences control expression of the coding sequences. Antisense oligonucleotides are typically between about 5 to about 100 nucleotides in length, more typically, between about 7 and about 50 nucleotides in length, and even more typically between about 10 nucleotides and about 30 nucleotides in length.

As used herein, the term "nucleic acid" or a "nucleic acid molecule" refer to any DNA or RNA molecule, either single or double stranded, whether in linear or circular form. With reference to nucleic acids of the present invention, the term "isolated nucleic acid", when applied to DNA or RNA, refers to a DNA or RNA molecule that is separated from sequences with which it is immediately contiguous in the naturally occurring genome or gene products of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

As used herein, the terms "specifically hybridizing" or "substantially complementary" refer to the association between two nucleotide molecules of sufficient complementarity to permit hybridization under pre-determined conditions generally used in the art. Examples of low, middle or intermediate and high stringency hybridization conditions are well known to the skilled artisan, e.g., using Sambrook and Russell, 2012, Molecular Cloning, A Laboratory Approach, Cold Spring Harbor Press, Cold Spring Harbor, N.Y., or Ausubel et al., 2012, Current Protocols in Molecular Biology, John Wiley & Sons, NY, relevant portions incorporated herein by reference.

As used herein, the phrase "chemically modified oligonucleotide" refers to a short nucleic acid (DNA or RNA) that can be a sense or antisense that includes modifications or substitutions, such as those taught by Wan and Seth, "The Medicinal Chemistry of Therapeutic Oligonucleotides", J. Med. Chem. 2016, 59, 21, 9645-9667, relevant portions incorporated wherein, which may include modifications of: (1) the ribose or other sugar units, (2) bases, or (3) the backbone, which in nature is composed of phosphates, as are known in the art. Non-limiting examples of modifications or nucleotide analogs include, without limitation, nucleotides with phosphate modifications comprising one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions (see, e.g., Hunziker and Leumann (1995) Nucleic Acid Analogues: Synthesis and Properties, in Modern Synthetic Methods, VCH, 331-417; Mesmaeker et al. (1994) Novel Backbone Replacements for Oligonucleotides, in Carbohydrate Modifications in Antisense Research, ACS, 24-39); nucleotides with modified sugars (see, e.g., U.S. Patent Application Publication No. 2005/0118605) and sugar modifications such as 2'-O-methyl (2'-O-methylnucleotides) and 2'-O-methyloxyethoxy (2'-O-MOE), a 2'-O-alkyl modified sugar moiety, or a bicyclic sugar moiety, and nucleotide mimetics such as, without limitation, peptide nucleic acids (PNA), morpholino nucleic acids, cyclohexenyl nucleic acids, anhydrohexitol nucleic acids, glycol nucleic acid, threose nucleic acid, and locked nucleic acids (LNA), as well as partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, and a combinations of two or more of any of the foregoing (see, e.g., U.S. Pat. Nos. 5,886,165; 6,140,482; 5,693,773; 5,856,462; 5,973,136; 5,929,226; 6,194,598; 6,172,209; 6,175,004; 6,166,197; 6,166,188; 6,160,152; 6,160,109; 6,153,737; 6,147,200; 6,146,829; 6,127,533; and 6,124,445, relevant portions incorporated herein by reference).

As used herein, the term "expression cassette" refers to a nucleic acid molecule comprising a coding sequence operably linked to promoter/regulatory sequences necessary for transcription, processing and, optionally, translation or splicing of the coding sequence.

The IL7R SM-ASOs that decrease sIL7R can be used for the treatment of diseases or disorders such as autoimmune and/or inflammatory diseases. The IL7R SM-ASOs that increase sIL7R can be used for immuno-oncology applications. Whether increasing or decreasing the expression of sIL7R message or protein, the present invention can used be used in conjunction with gene therapy and ex vivo applications. For example, the oligonucleotides can be used in a method in which cells are isolated from the subject or another subject, and the cells are modified to express the oligonucleotides that modify the expression of sIL7R, and the cells can then be transferred back into the subject. The present invention can be used with the various known methods of delivery and expression, such as plasmid or viral vectors. Also, the present invention can be used with all methods for modification of cells, e.g., gene editing, delivery of nucleic acids (any nucleic acid, either natural, synthetic or modified), proteins (full-length protein or peptides), whether transient or permanent, or under the control of regulatable promoters. The oligonucleotide or vectors that express the same can be delivered via known methods, such as, e.g., transfection, electroporation, carrier-mediated, viral, etc.

As used herein, the term "promoter/regulatory sequence" refers to a nucleic acid sequence that is required for expression of a gene product operably linked to the promoter/regulator sequence. In some instances, the promoter/regulatory sequence may be the core promoter sequence and in other instances, this sequence may also include an enhancer sequence and other regulatory elements that are required for expression of the gene product. The promoter/regulatory sequence may be, for example, a sequence that drives the expression of a gene product in a constitutive and/or inducible manner. As used herein, the term "inducible promoter" refers to a nucleotide sequence which, when operably linked with a polynucleotide which encodes or specifies a gene product, causes the gene product to be produced substantially only when an inducer which corresponds to the promoter is present.

As used herein, the terms "percent similarity", "percent identity" and "percent homology", when referring to a comparison between two specific sequences, identify the percentage or bases that are the same along a particular sequence. The percentage of similarity, identity or homology can be calculated using, e.g., the University of Wisconsin GCG software program or equivalents.

As used herein, the term "replicon" refers to any genetic element, for example, a plasmid, cosmid, bacmid, phage or virus, which is capable of replication largely under its own control. A replicon may be either RNA or DNA and may be single or double stranded.

As used herein, the term "vector" refers to a genetic element, such as a plasmid, cosmid, bacmid, phage or virus, to which another genetic sequence or element (either DNA or RNA) may be attached. The vector may be a replicon so as to bring about the replication of the attached sequence or element. An "expression vector" is a vector that facilitates the expression of a nucleic acid, such as an oligonucleotide, or a polypeptide coding nucleic acid sequence in a host cell or organism.

As used herein, the term "operably linked" refers to a nucleic acid sequence placed into a functional relationship with another nucleic acid sequence. Examples of nucleic acid sequences that may be operably linked include, without limitation, promoters, transcription terminators, enhancers or activators and heterologous genes which when transcribed and, if appropriate to, translated will produce a functional product such as a protein, ribozyme or RNA molecule.

As used herein, the term "oligonucleotide," refers to a nucleic acid strand, single or double stranded that has a length that is, typically, less than a coding sequence for a gene, e.g., the oligonucleotide will generally be at least 4-6 bases or base-pairs in length, and up to about 200, with the most typical oligonucleotide being in the range of 8-20, 10-25, 12-30, or about 30, 35, 40, or 50 bases or base-pairs. In one specific example of the present invention, the oligonucleotide is a nucleic acid strand having a sequence that modulates the inclusion of exon 6 in pre-mRNAs of the Interleukin-7 receptor (IL7R) gene, and is defined as a nucleic acid molecule comprised of two or more ribo or deoxyribonucleotides, preferably more than four. The exact size of the oligonucleotide will depend on various factors and on the particular application and use of the oligonucleotide, which can be varied as will be known to the skilled artisan without undue experimentation following the teachings herein and as taught in, e.g., Sambrook and Russell, 2012, Molecular Cloning, A Laboratory Approach, Cold Spring Harbor Press, Cold Spring Harbor, N.Y., or Ausubel et al., 2012, Current Protocols in Molecular Biology, John Wiley & Sons, NY, relevant portions incorporated herein by reference.

As used herein, the term "splice variant or isoform of an mRNA", is meant a variant mRNA, which could be defective or pathogenic and be the result of alternative splicing of the RNA encoding a protein. Splicing events that produce a splice variant of the mRNA that is defective or leads to pathology will be referred in the present invention as a splicing defect. One example of such a splicing defect is the exclusion of exon 6 of IL7R causing expression of a shorter protein, soluble IL7R (sIL7R), which is secreted from the cell, leading to its presence in, e.g., the bloodstream or other bodily fluids. The present invention targets the elements (i.e., sequences) within IL7R pre-mRNAs that control the inclusion or exclusion of IL7R exon 6 in the final mature or processed mRNA, or sequences within sIL7R mRNA that control its translation or stability.

As used herein, the term "splice variant or isoform of a protein", is meant a variant protein, which could be defective or pathogenic and be the result of alternative splicing of an RNA encoding a protein. Alternatively, when discussing those variants that increase degradation, those splice variants would reduce or eliminate protein production. Splicing events that produce a splice variant of a protein that is defective or leads to pathology will be referred in the present invention as a splicing defect. One example of such a splicing defect is the exclusion of exon 6 of IL7R causing expression of a shorter protein, soluble IL7R (sIL7R), which is secreted from the cell, leading to its presence in, e.g., the bloodstream or other bodily fluids. The present invention targets the elements (i.e., sequences) within IL7R pre-mRNAs that control the inclusion or exclusion of IL7R exon 6 in the final mature or processed mRNA, or sequences within sIL7R mRNA that control its translation or stability.

As used herein, the term "treatment", refers to reversing, alleviating, delaying the onset of, inhibiting the progress of, and/or preventing a disease or disorder, or one or more symptoms thereof, to which the term is applied in a subject, e.g., an autoimmune disease or disorder. In some embodiments, the treatment may be applied after one or more symptoms have developed. In other embodiments, treatment may be administered in the absence of symptoms. For example, treatment may be administered prior to symptoms (e.g., in light of a history of symptoms and/or one or more other susceptibility factors), or after symptoms have resolved, for example to prevent or delay their reoccurrence. One such non-limiting example is relapsing-remitting MS.

As used herein, the terms "effective amount" and "pharmaceutically effective amount" refer to a sufficient amount of an agent to provide the desired biological result. Preferably, the sufficient amount of the agent does not induce toxic side effects. The present invention using IL7R SM-ASOs that reduce sIL7R should lead to a reduction and/or alleviation of the signs, symptoms, or causes of autoimmune diseases or disorders. As designed, the present invention is not expected to cause a reduction in the host immune response, and thus have few or low side effects associated with broad immunosuppression. An appropriate effective amount in any individual case may be determined by one of ordinary skill in the art using routine experimentation. The present invention using IL7R SM-ASOs that increase sIL7R should lead to a reduction and/or alleviation of the signs, symptoms, or causes of cancers. As designed, the present invention is expected to cause an enhancement in the host immune response and thus to enhance current immunotherapies. An appropriate effective amount in any individual case may be determined by one of ordinary skill in the art using routine experimentation.

The present invention may be provided in conjunction with one or more "pharmaceutically acceptable" agents, carriers, buffers, salts, or other agents listed in the U.S. Pharmacopeia or other generally recognized pharmacopeia for use in animals, and more particularly in humans, which generally indicates approval by a regulatory agency of the Federal government or a state government. Typical pharmaceutically acceptable formulations for use with oligonucleotides include but are not limited to salts such as: calcium chloride dihydrate (US Pharmacopeia (USP)), magnesium chloride hexahydrate USP, potassium chloride USP, sodium chloride USP; and may include buffers such as" sodium phosphate dibasic anhydrous USP, sodium phosphate monobasic dihydrate USP, and water USP. Typically, the pH of the product may be modified using hydrochloric acid or sodium hydroxide to a pH of ~6.8, 6.9, 7.0, 7.1, or 7.2.

The present invention may be provided in conjunction with one or more diagnostic tests that are used to demonstrate the effectiveness of the treatment.

As used herein, the term "carrier" refers to, for example, a diluent, preservative, solubilizer, emulsifier, adjuvant, excipient, auxiliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions may be employed as carriers. Suitable pharmaceutical carriers are described in "Remington's Pharmaceutical Sciences" 2012.

In one embodiment, the present invention is directed to novel compositions and methods to treat autoimmune disorders, including but not limited to Multiple Sclerosis (MS). MS is the most common neurological disease of early adulthood and is mediated by autoimmune mechanisms that lead to demyelination and neuronal damage in the central nervous system, resulting in progressive neurological dysfunction. To date, there is no cure for the disease and current available treatments focus on preventing future immunological attacks, often by suppressing the immune system. This immunosuppressive approach causes a plethora of adverse side effects, among them increased risk of cancer and infections that could be severe or lethal. Accordingly, the present inventors have developed novel therapeutics to meet the clear, unmet need for the development of effective and well-tolerated therapies to arrest MS development, without adverse immunosuppressive side effects.

The present invention is also directed to novel compositions and methods to treat cancer. Cancer is the second cause of death in the United States and is mediated by many etiologies. To date, many cancers cannot be treated; however, recently therapies based on immune recognition and killing of cancer cells have led to new hope. Unfortunately, many patients receiving immunotherapy do not respond well and some cancer types (e.g., hepatocellular carcinoma) have low response rates. Accordingly, the present inventors have developed novel therapeutics to meet the clear, unmet need for the enhancement of conventional immunotherapies.

The present inventors have developed targeted antisense oligonucleotides, such as antisense oligonucleotides (ASOs) and/or splice-modulating antisense oligonucleotides (SM-ASOs), to correct a specific MS etiology. SM-ASOs have proven to be a novel and valuable therapeutic tools to treat disorders caused by aberrant RNA splicing. Two such SM-ASOs have received recent approvals by the FDA for treatment of Spinal Muscular Atrophy (Spinraza, Biogen) and Duchenne Muscular Dystrophy (Exondys 51, Sarepta Therapeutics).

The novel targeted therapeutics correct aberrant splicing of the interleukin 7 receptor (IL7R) RNAs, where exclusion of the alternative exon 6 leads to elevated levels of the pathogenic soluble form of the IL7R (sIL7R). Several lines of evidence directly link and strongly support a role for alternative splicing of IL7R exon 6 in the pathogenesis of MS and other autoimmune diseases: (1) genetic variants that increase exclusion of this exon are strongly associated with increased MS risk (Galarza-Munoz et al., 2017; Gregory et al., 2007); (2) sIL7R exacerbates the severity and progression of the disease in the Experimental Autoimmune Encephalomyelitis (EAE) mouse model of MS (Lundstrom et al., 2013); and (3) sIL7R is elevated in patients from several autoimmune diseases including MS, type I diabetes, rheumatoid arthritis and systemic lupus erythematosus (Badot et al., 2011; Badot et al., 2013; Lauwerys et al., 2014; McKay et al., 2008; Monti et al., 2013).

The present inventors have developed several SM-ASOs (Table 1), among them the lead ASOs IL7R-005 and IL7R-006, that promote inclusion of exon 6 in IL7R pre-mRNAs and correct expression of IL7R protein isoforms in cultured cells. Critical to this therapeutic approach, these SM-ASOs decrease sIL7R levels without a negative impact on expression of the membrane-bound IL7R (mIL7R). To treat autoimmunity, the present invention is used to block specific sequences in IL7R pre-mRNAs that drive exon 6 exclusion, thereby promoting exon 6 inclusion and reducing sIL7R levels. Additionally, to treat cancer, the present invention is used to block specific sequences in IL7R pre-mRNAs that drive exon 6 inclusion, thereby decreasing exon 6 inclusion and increasing sIL7R levels. The skilled artisan will recognize that the SM-ASOs of the present invention can be used alone or in combination with other therapies. Furthermore, through simple single base mutation, the SM-ASOs can be adapted to control splicing of exon 6 in allelic variants of human IL7R, or of IL7R in different animals, or in individuals carrying polymorphisms or where mutations have occurred at the targeted sequences, thus tailoring the complementarity of the SM-ASOs to the variant sequences.

TABLE 1

Target sequence of SM-ASOs that reduce sIL7R.

| SM-ASO | Target Sequence* | Efficiency^ | Disease application | SEQ ID NO: |
|---|---|---|---|---|
| IL7R-005 | GUCGCUCUGUUGGUC | +++ | Autoimmunity | 1 |
| IL7R-006 | UAAUAAAGAGGGUGAUUGUG | +++ | Autoimmunity | 2 |
| IL7R-008 (Cluster 2) | UUGUGUGGGAUCACG | +++ | Autoimmunity | 3 |
| IL7R-009 (Cluster 2) | UGGGAUCACGGACAG | +++ | Autoimmunity | 4 |
| IL7R-010 (Cluster 2) | UCACGGACAGUCAGA | +++ | Autoimmunity | 5 |
| Cluster 2 | UUGUGUGGGAUCACGGACAGUCAGA | +++ | Autoimmunity | 6 |
| IL7R-011 | GACAGUCAGAGCUUAAGC | + | Autoimmunity | 7 |
| IL7R-017 | UGAGAAAACCACAAA | ++ | Autoimmunity | 8 |
| IL7R-024 | UACCCCACUGCAUG | + | Autoimmunity | 9 |
| IL7R-025 (Cluster 1) | GACCCUACCCCCACU | +++ | Autoimmunity | 10 |
| IL7R-026 (Cluster 1) | CCUGAGACCCUACCC | +++ | Autoimmunity | 11 |
| IL7R-027 (Cluster 1) | AGCACCCUGAGACCC | +++ | Autoimmunity | 12 |
| Cluster 1 | AGCACCCUGAGACCCUACCCCCACU | +++ | Autoimmunity | 13 |

*Nucleotides highlighted in bold and underlined indicate positions were a mismatch was engineered at the complementary position in the SM-ASO to disrupt potential secondary structures that could limit the activity of the SM-ASO.
^Efficacy scale: low (+), intermediate (++), and high (+++).

A wide variety of SM-ASOs can be used with the present invention, e.g., those that include a wide variety of base or backbone modifications to the SM-ASOs. Non-limiting examples of SM-ASOs can include native nucleic acids, but can also include, e.g., backbone or base modifications (chemically modified oligonucleotides) that increase the efficiency of binding of the SM-ASO, increase the stability (e.g., half-life) of the SM-ASO, increase its expression, control where its expressed, distributed or localized, and the like.

Current treatments for autoimmune diseases, such as MS, have helped autoimmune disease patients manage their symptoms, yet these drugs are far from ideal given the wide variety of adverse side effects they cause, which can be severe or lethal. The development of effective but yet safer MS drugs has been hindered by the complex nature of the disease, wherein a multitude of etiologies lead to MS pathogenesis. Given that all these etiologies culminate in a breach of immunological tolerance against myelin, the field has, so far, focused on developing therapies to diminish immunological responses via diverse mechanisms. For example, natalizumab is designed to block migration of leukocytes across blood-brain barrier and their recruitment to sites of inflammation. Another example is ocrelizumab, which depletes B-cells. However, both of these mechanisms (although through different actions) ultimately lead to immunosuppression. In order to provide effective yet safer drugs to the patients, instead of dealing with the consequences of a given etiology via immune modulation, it is imperative to develop new therapies targeting correction of specific MS etiologies, which the present inventors refer to herein as immune correction.

The canonical, membrane-bound interleukin 7 receptor (mIL7R) has been a previous candidate of therapeutic intervention in MS and numerous autoimmune disorders. However, mIL7R is crucial for T cell homeostasis and normal immune function, and loss of IL7R function in both human and mouse cause severe immunodeficiency (Maraskovsky et al., 1996; Peschon et al., 1994; Puel et al., 1998; Roifman et al., 2000). Accordingly, novel MS therapies that inhibit expression or function of mIL7R would cause severe immunodeficiency. The therapeutic SM-ASOs developed here correct aberrant splicing of IL7R exon 6, and in doing so, they diminish sIL7R levels while preventing a negative impact on mIL7R expression and/or function. Accordingly, unlike current MS treatments relying on immunosuppressive mechanisms, the therapeutic SM-ASOs of the present invention that reduce sIL7R (Table 1) are an effective and safer option to treat MS that avoid immunosuppression. The SM-ASOs of the present invention that reduce sIL7R (Table 1) represent a major improvement over current drugs in that they correct the root of the problem rather than deal with the consequences of it by suppressing the immune system.

Furthermore, increased levels of sIL7R (when compared to the normal levels of sIL7R in subject that does not have an autoimmune disease) has been associated with other autoimmune diseases such as type I diabetes, rheumatoid arthritis and systemic lupus erythematosus, and patients of these diseases have been shown to have elevated levels of circulating sIL7R (Badot et al., 2011; Badot et al., 2013; Lauwerys et al., 2014; Monti et al., 2013). Therefore, the therapeutic SM-ASOs could be used to treat numerous diseases or disorders that have elevated levels of sIL7R.

Cancer is the second leading cause of death in the United States. Effective treatment options for many cancers are lacking given the many etiologies that orchestrate it. Immuno-oncology is a rapidly growing field that uses the body's immune system as novel treatments for previously intractable cancers. Immune check point inhibitors, such as monoclonal antibodies that target the negative immune regulators CTLA-4 (Ipilimumab (Yervoy, Bristol-Myers Squibb) and PD-1 (Pembrolizumab (Keytruda, Merck) and Nivolumab (Opdivo, Bristol-Myers Squibb) are FDA approved. An example their potential is the study in patients with previously untreated, and inoperable or metastatic melanoma who were treated with a combination of Nivolumab and Ipilimumab, which reported a 50% overall response rate (Larkin J, Chiarion-Sileni V, Gonzalez R, Grob J J, Cowey C L, et al. 2015. N Engl J Med 373: 23-34).

Although recent cancer immunotherapies have provided new hope, unfortunately, many patients receiving immunotherapy do not respond well and some cancer types (e.g., hepatocellular carcinoma) have low response rates. For instance, while Nivolumab is FDA-approved for patients with hepatocellular carcinoma who failed to respond to the kinase inhibitor Sorafenib, the overall response rate among 154 patients tested was only 14.3% and a complete response was observed in only 3 patients (NCT01658878). Although encouraging, these data indicate that there is a critical need to increase the response rate.

The need to increase immunotherapeutic response rate has inspired the intense search for markers (e.g., PD-L1 expression and high microsatellite instability in tumor cells) that predict success for the currently deployed immune check point blockers. Equally exciting, although less developed, is the search for pro-immune modulators that could synergize with check point blockade. Elevated levels of sIL7R are thought to enhance immunological responses by potentiating the bioavailability and/or bioactivity of the cytokine IL7, leading to enhanced survival of T cells (Lundstrom et al., 2013). This creates a pro-inflammatory environment that has the potential to increase immune responses against cancers. Accordingly, the present invention uses SM-ASOs that increase sIL7R, such as lead SM-ASOs IL7R-001 and IL7R-004, and additional SM-ASOs in Table 2, as a novel immunotherapy against cancer.

TABLE 2

Target sequence of SM-ASOs that increase sIL7R.

| SM-ASO | Target Sequence* | Eff-iciency^ | Disease application | SEQ ID NO |
|---|---|---|---|---|
| IL7R-001 | AGGUGACCUUCUUCAACUAAUAAAG | +++ | Immuno-oncology | 14 |
| IL7R-002 | CAUCAGCAUUUUGAG | +++ | Immuno-oncology | 15 |
| IL7R-003 | UUUUUUCUCUGUCGCUCUGUUGGUC | +++ | Immuno-oncology | 16 |
| IL7R-004 | UCUCUGUCGCUCUGU | +++ | Immuno-oncology | 17 |
| IL7R-007 | GGUGAUUGUGUGGGA | + | Immuno-oncology | 18 |
| IL7R-013 | GCUUAAGCCCCAUUUAUUGAUG | + | Immuno-oncology | 19 |

TABLE 2-continued

Target sequence of SM-ASOs that increase sIL7R.

| SM-ASO | Target Sequence* | Efficiency^ | Disease application | SEQ ID NO |
|---|---|---|---|---|
| IL7R-015 | CAUUUAUUGAUGAGAAAACCA | +++ | Immuno-oncology | 20 |
| IL7R-018 | AAACCACAAAGGGGA | ++ | Immuno-oncology | 21 |
| IL7R-019 | ACAAAGGGGAUUAAGG | +++ | Immuno-oncology | 22 |
| IL7R-020 | GGGGAUUAAGGCAUUUCA | ++ | Immuno-oncology | 23 |
| IL7R-021 | UUAAGGCAUUUCACGA | + | Immuno-oncology | 24 |
| IL7R-023 | UCACGAAUUUAGUGCC | + | Immuno-oncology | 25 |
| IL7R-031 | CCCACAUUACUAAGUAAA | + | Immuno-oncology | 26 |
| IL7R-032 | GGCCCACAUUACUAA | ++ | Immuno-oncology | 27 |
| IL7R-033 | AAGUGGGCCCACAUU | + | Immuno-oncology | 28 |
| IL7R-034 | AUAAUAAGUGGGCCC | + | Immuno-oncology | 29 |
| IL7R-039 | UCUCUUAACUGAAAAGCAA | + | Immuno-oncology | 30 |
| IL7R-042 | CAAAUAUGUCUCUUAACUGAAA | +++ | Immuno-oncology | 31 |
| IL7R-043 | UGUCAAAUAUGUCUCUUAAC | ++ | Immuno-oncology | 32 |
| IL7R-044 | GCUGUCAAAUAUGUCUC | + | Immuno-oncology | 33 |
| IL7R-045 | AUAAAGCUGUCAAAUAU | + | Immuno-oncology | 34 |
| IL7R-046 | UCCAUAAAGCUGUCA | ++ | Immuno-oncology | 35 |
| IL7R-047 | AUCCCUCCAUAAAGC | + | Immuno-oncology | 36 |
| IL7R-048 | AACCAAAAUCCCUCCAU | ++ | Immuno-oncology | 37 |
| IL7R-049 | UGCCUUUUAAACCAAAAUCCC | +++ | Immuno-oncology | 38 |
| IL7R-050 | GUCAAUGCCUUUUAAACCAAA | ++ | Immuno-oncology | 39 |
| IL7R-051 | CCCAAGUCAAUGCCUUUUAAA | + | Immuno-oncology | 40 |
| IL7R-053 | GUCACCCAAGUCAAU | + | Immuno-oncology | 41 |
| IL7R-054 | GCCUGGUCACCCAAG | + | Immuno-oncology | 42 |
| IL7R-058 | AAUUUAGUGCCCAGU | + | Immuno-oncology | 43 |
| IL7R-059 | AGUGCCCAGUAUCCC | ++ | Immuno-oncology | 44 |
| IL7R-060 | CCAGUAUCCCUAUCU | ++ | Immuno-oncology | 45 |
| IL7R-061 | AUCCCUAUCUAUCCUCA | ++ | Immuno-oncology | 46 |
| IL7R-062 | UAUCUAUCCUCAGCG | + | Immuno-oncology | 47 |
| IL7R-063 | AUCCUCAGCGAAUUUC | + | Immuno-oncology | 48 |
| IL7R-064 | CAGCGAAUUUCCACA | + | Immuno-oncology | 49 |
| IL7R-065 | AAUUCCACAGUUAAUUUCAUAAG | ++ | Immuno-oncology | 50 |

*Nucleotides highlighted in bold and underlined indicate positions were a mismatch was engineered at the complementary position in the SM-ASO to disrupt potential secondary structures that could limit the activity of the SM-ASO.
^Efficacy scale: low (+), intermediate (++), and high (+++).

Figure 1B:
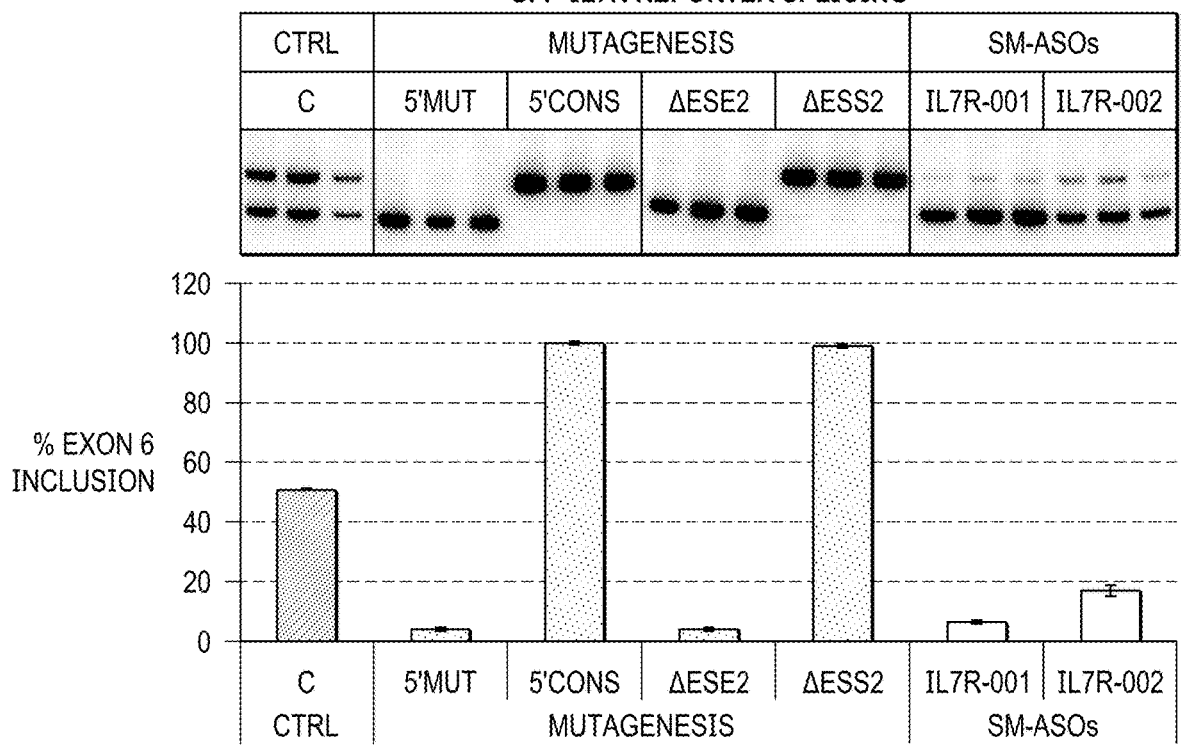
Figure 1C:
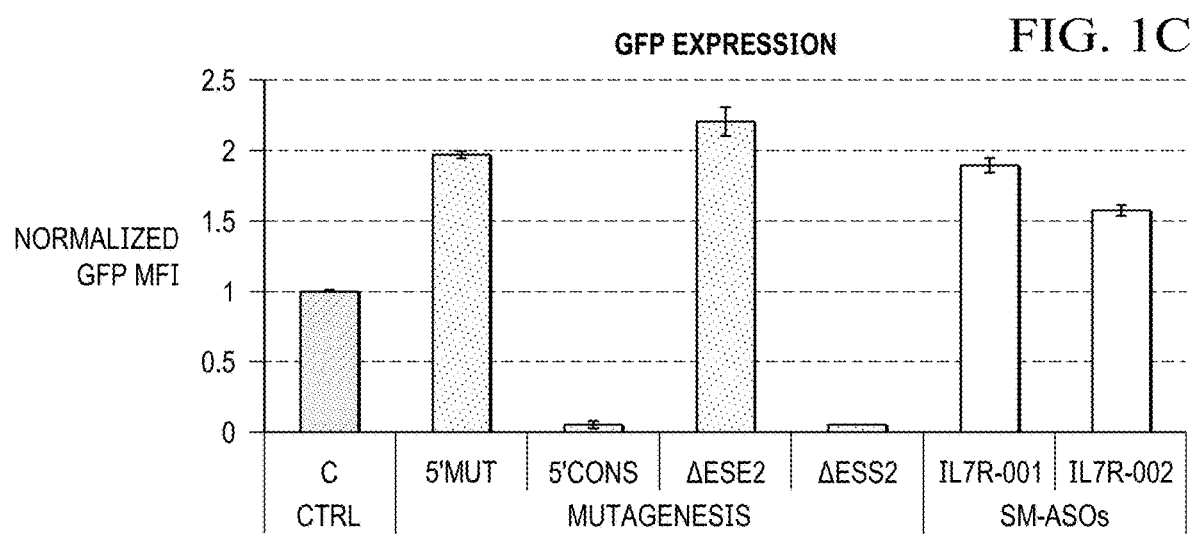

FIGS. 1A to 1C show validation of a GFP-IL7R fluorescent splicing reporter for screening of splice-modulating antisense oligonucleotides (SM-ASOs). FIG. 1A shows schematics of the GFP-IL7R reporter illustrating location of SM-ASO targets (red) and mutations of the corresponding cis-splicing elements (blue). FIG. 1B shows splicing analysis of IL7R exon 6 in transcripts from the GFP-IL7R reporter. Hela cells stably expressing either WT (C) or mutant versions of the reporter (5'Mut, 5'Cons, AESE2 & AESS2) were transfected with either control (Ctrl) or experimental (IL7R-001 & IL7R-002) SM-ASOs. Exon 6 splicing was analyzed by RT-PCR using primers specific for the GFP-IL7R reporter (+E6=exon 6 included; E6=exon 6 excluded), and percentage of exon 6 inclusion was calculated as: [included/(included+excluded)]*100. FIG. 1C shows analysis of GFP expression. GFP mean fluorescence intensity (MFI) was quantified by flow cytometry. Data are shown normalized to control SM-ASO (Ctrl).

To assess the feasibility of this reporter system to screen for SM-ASOs that modulate splicing of IL7R exon 6, the present inventors compared the effects of blocking specific cis-acting splicing elements in exon 6 with mutation of the corresponding elements. For example, SM-ASO IL7R-001 blocks the 5'-splice site of exon 6 and forces almost complete exclusion of the exon equivalent to a mutation that cripples this 5'-splice site (5'Mut). Likewise, blocking of the previously identified exonic splicing enhancer 2 (ESE2) by IL7R-002 causes comparable effects than mutation of this enhancer (AESE2). IL7R-002 has low affinity for IL7R RNAs, which likely explains the slightly lower magnitude compared to ΔESE2. The fact that SM-ASO-mediated blocking or mutation of a given cis-splicing element caused equivalent effects demonstrates the power of SM-ASOs to control splicing decisions in this reporter system. More importantly, the observed changes in exon 6 splicing lead to the expected changes in GFP expression, thereby validating the use of GFP expression as readout of splicing outcomes in this reporter system.

Figure 2A:
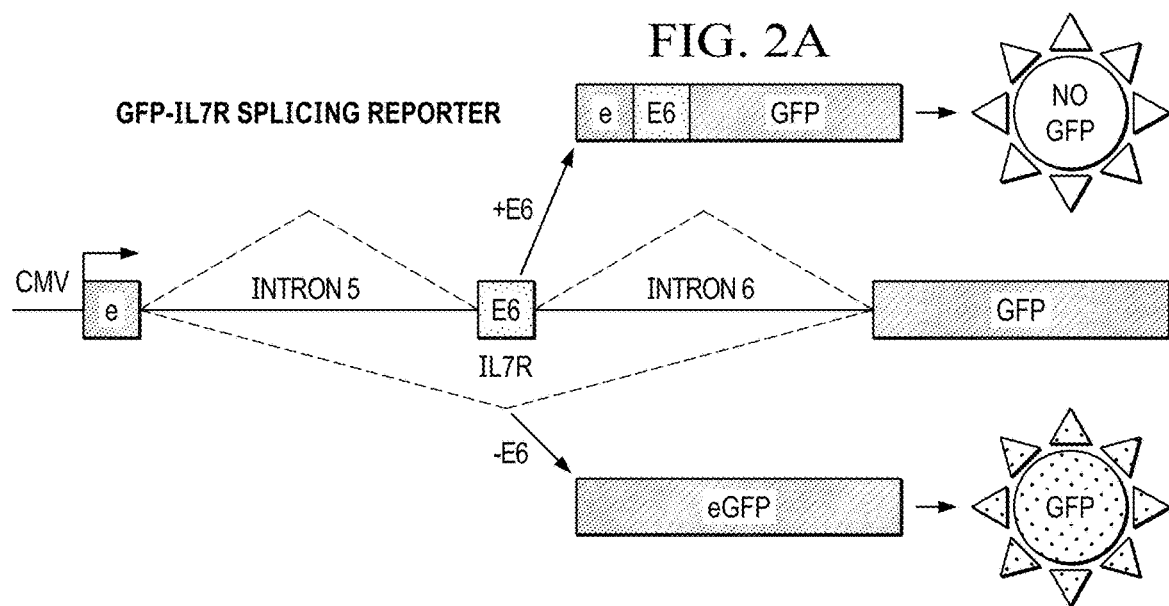
FIGS. 2A to 2E show the targeted screening of IL7R splice-modulating antisense oligonucleotides (SM-ASOs) complementary to sequences in exon 6.
Figure 2B:
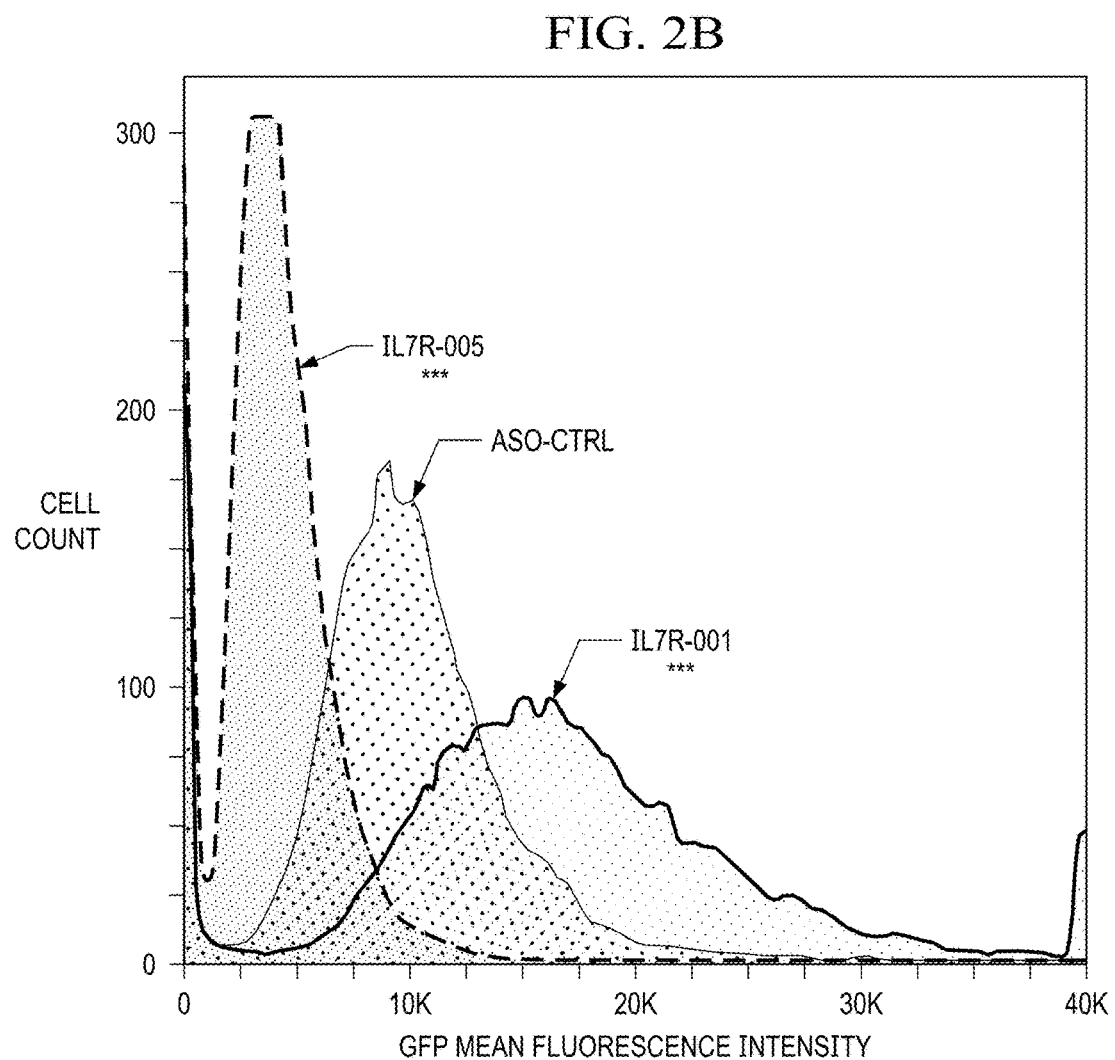
Figure 2C:
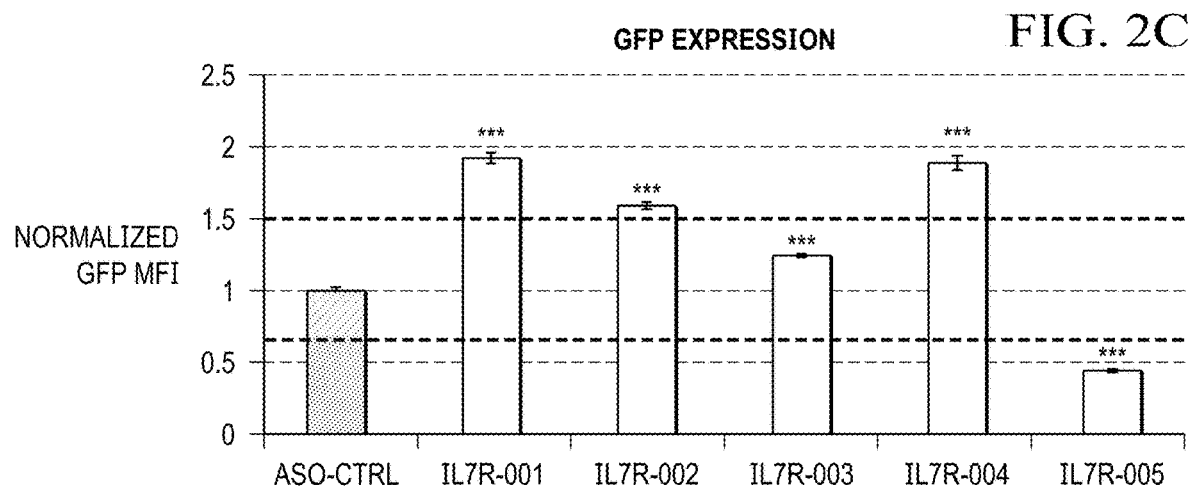
Figure 2D:
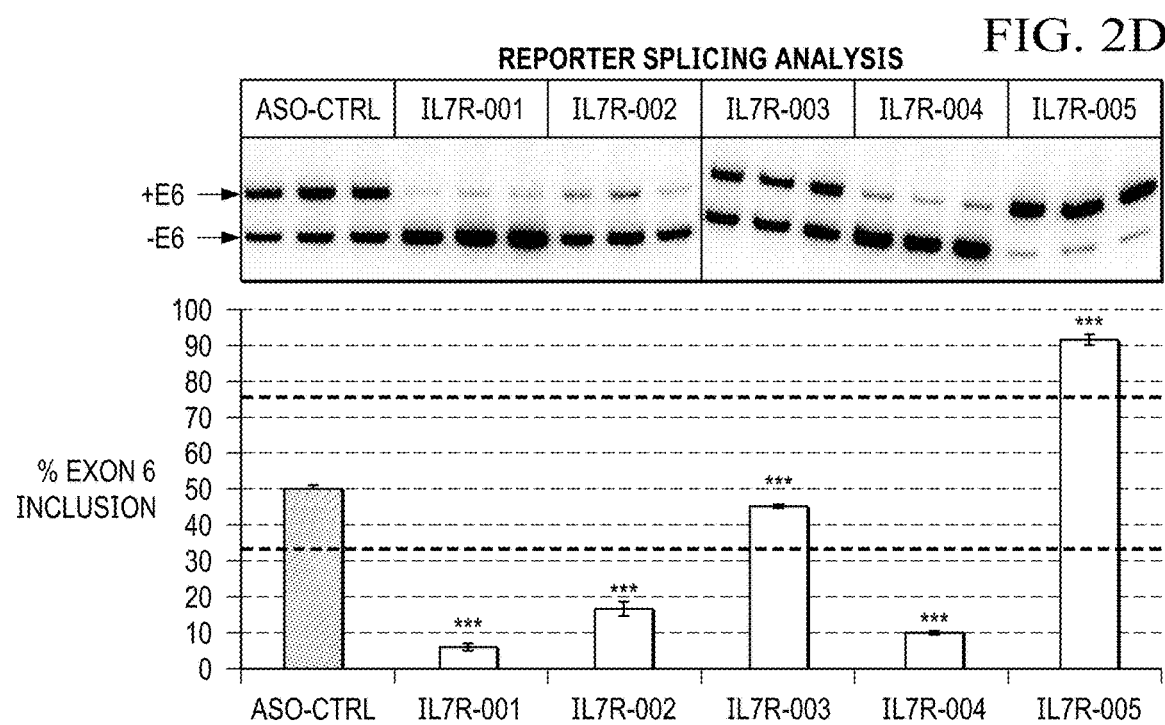
Figure 2E:
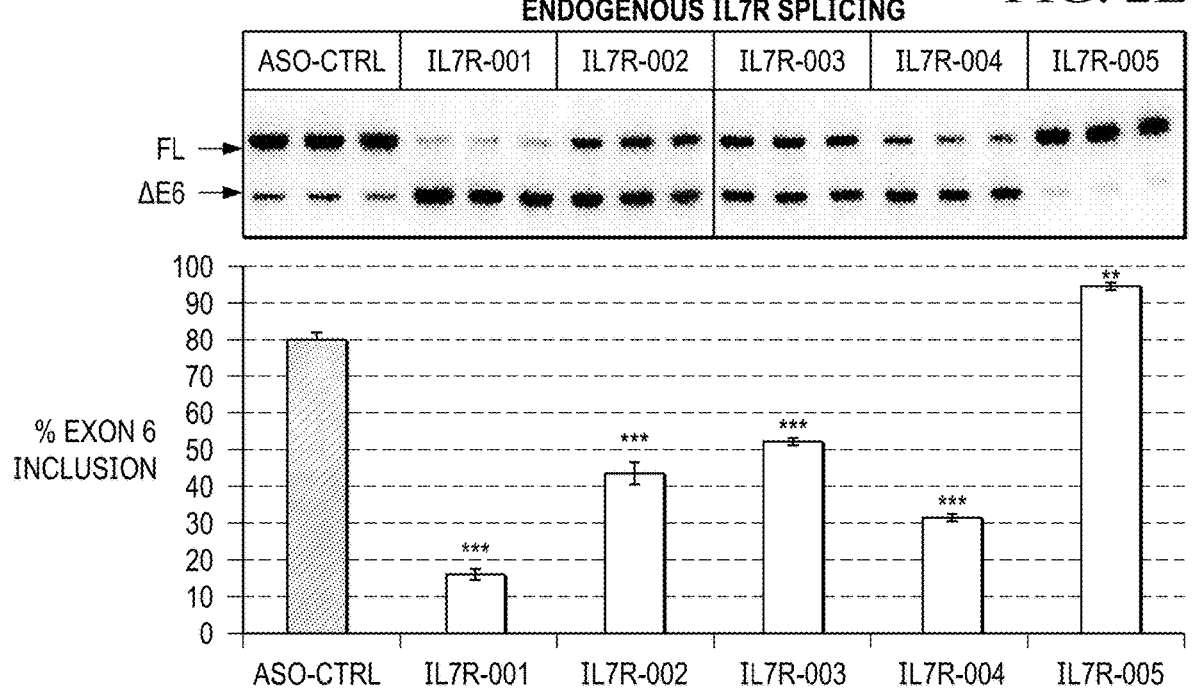

FIGS. 2A to 2E shows a targeted screening of IL7R SM-ASOs complementary to cis-acting splicing elements within exon 6. FIG. 2A shows schematics of the GFP-IL7R splicing fluorescent reporter used for screening. The genomic sequence of IL7R spanning introns 5 and 6 was cloned interrupting the GFP coding sequence, so that GFP expression is determined by splicing of IL7R exon 6. FIGS. 2B and 2C show analysis of GFP expression. HeLa cells stably expressing the fluorescent reporter were transfected with either control (ASO-Ctrl) or experimental morpholino SM-ASOs (IL7R-001-IL7R-005), and GFP expression was quantified by flow cytometry. FIG. 2B shows representative histograms of GFP mean fluorescence intensity (MFI) for selected SM-ASOs, whereas FIG. 2C shows quantification of GFP MFI normalized to control ASO (ASO-ctrl). Red dashed lines indicate efficacy cutoff of 1.5 fold change in GFP expression in either direction. FIG. 2D shows splicing analysis of IL7R exon 6 in transcripts from the GFP-IL7R reporter. Splicing of IL7R exon 6 was analyzed in transcripts from the reporter by RT-PCR using primers specific for the GFP-IL7R reporter (+E6=exon 6 included; −E6=exon 6 excluded), and percentage of exon 6 inclusion was determined as: [included/(included+excluded)]*100. Red dashed lines indicate efficacy cutoff of 1.5 fold change in percentage of exon 6 inclusion. FIG. 2E shows splicing analysis of IL7R exon 6 in transcripts from the endogenous IL7R gene. Splicing of IL7R exon 6 was analyzed in transcripts from the endogenous IL7R gene with primers specific for the endogenous transcripts (FL=exon 6 included; ΔE6=exon 6 excluded), and percentage of exon 6 inclusion was determined as: [FL/(FL+ΔE6)]*100. In all panels, statistical significance was assessed by two-tailed Student's t-test comparing experimental ASOs versus control ($*p<0.05$, $p<0.005$, $*p<0.0005$).

This targeted screen uncovered several SM-ASOs that modulate splicing of IL7R exon 6 in either direction. For example, blocking of the 5'-splice site (IL7R-001) or the previously identified ESE2 (IL7R-002) induces almost complete exclusion of the exon. Most importantly, it uncovered IL7R-005, which blocks the exonic splicing silencer 3 (ESS3) promoting almost complete exon inclusion. This one SM-ASO was found to be particularly useful for the treatment of autoimmune diseases. In addition, the present inventors uncovered four SM-ASOs that enhance exon 6 exclusion (IL7R-001, IL7R-002, IL7R-003 and IL7R-004), which are candidates for immuno-oncology applications. Critical for therapeutic purposes, all SM-ASOs tested induced similar modulation of exon 6 splicing in transcripts from both the GFP-IL7R reporter and the endogenous IL7R gene.

Figure 3A:
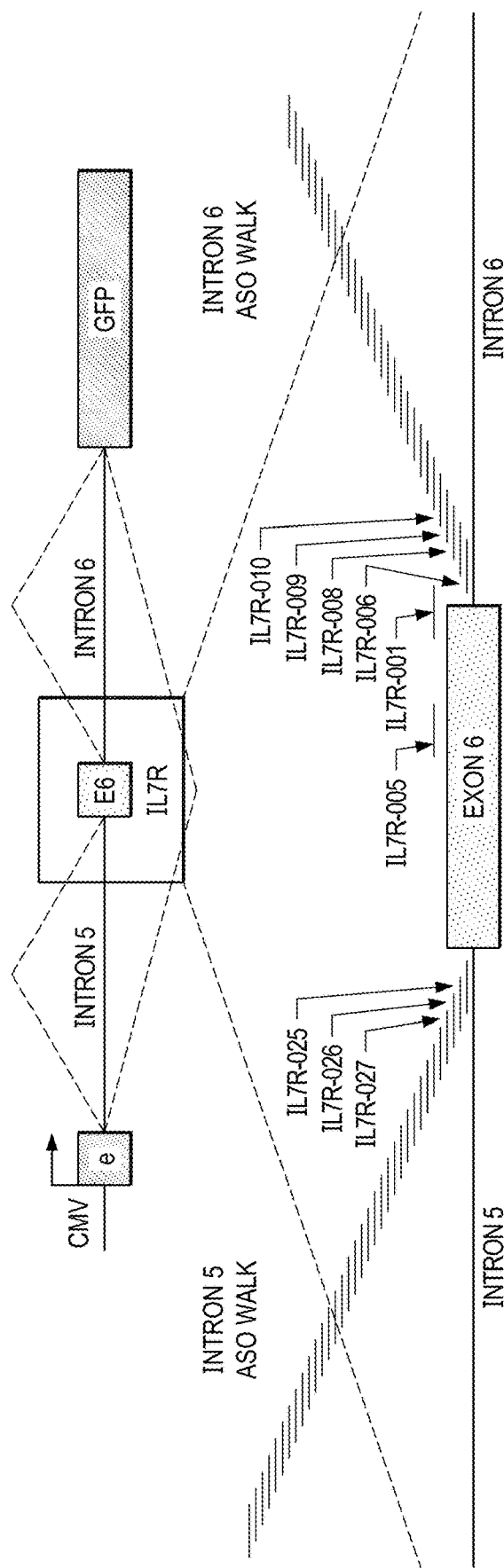
Figure 3E:
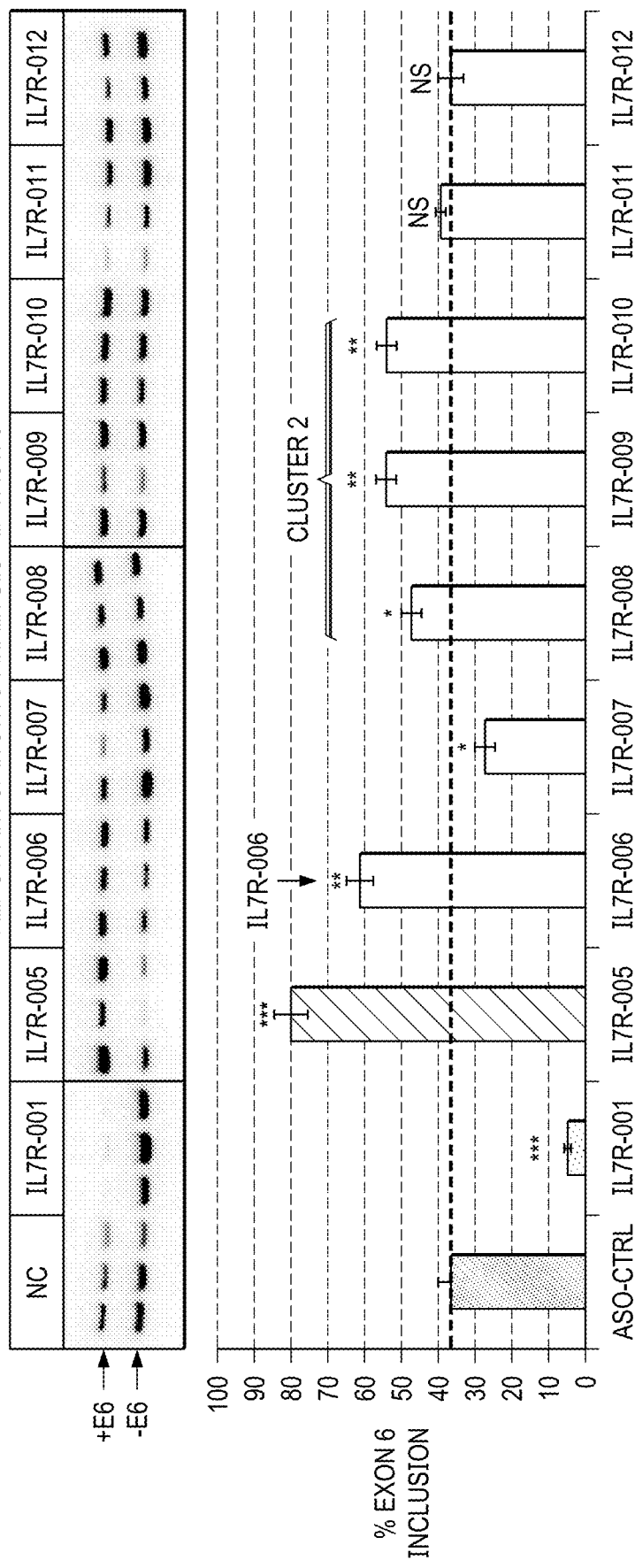

FIGS. 3A to 3E show an SM-ASO walk screen targeting sequences in IL7R introns 5 and 6. FIG. 3A shows the schematics of the SM-ASO walk approach. As an example, the present inventors designed morpholino SM-ASOs of 15-25 nt in length complementary to overlapping sequences every 5 nt within the intronic regions proximal to IL7R exon 6. These regions include the last 209 nt of IL7R intron 5, avoiding the last 40 nt which contain core splicing elements such as the branchpoint sequence, polypyrimidine tract and 3'-splice site, and the first 169 nt of IL7R intron 6, avoiding the first 15 nt which includes the 5'-splice site. Control (ASO-Ctrl) or experimental SM-ASOs targeting these intronic regions (e.g., IL7R-006-IL7R-065) were transfected into HeLa cells stably expressing the reporter system as in FIG. 2A. IL7R-001 and IL7R-005 were used as positive controls. FIGS. 3B and 3C show GFP expression analysis of SM-ASOs targeting introns 5 (FIG. 3B) and 6 (FIG. 3C). GFP mean fluorescence intensity (MFI) was determined by flow cytometry as before. Red and blue lines indicate cutoff of 20% decrease or increase in GFP MFI, respectively. FIGS. 3D and 3E show splicing analysis of IL7R exon 6 in transcripts from the GFP-IL7R reporter for selected SM-ASOs targeting introns 5 (FIG. 3D) and 6 (FIG. 3E). The percentage of exon 6 inclusion in transcripts from the reporter was determined as before. Red dash line indicates the level of exon 6 inclusion in the control (ASO-Ctrl). In all panels, statistical significance was assessed by two-tailed Student's t-test comparing experimental SM-ASOs versus control ($*p<0.05$, $p<0.005$, $*p<0.0005$).

This approach uncovered IL7R-006, another SM-ASO, which promotes high levels of exon 6 inclusion by blocking sequences within intron 6. Within the target sequence of SM-ASO IL7R-006 (UAAUAAAGAGGGUGAUUGUG) lies a poly adenylation signal (AAUAAA) near the 5' splice site of intron 6, which the inventors previously found to promote skipping of exon 6, most likely by blocking the 5'-splice site when bound by CPSF1 (Evsyukova et al., 2013). However, the IL7R-006 oligonucleotide of the present invention blocks a 20 nt sequence that contains additional splicing regulatory sequences, which is different from results published in Evsyukova et al., 2013.

In addition to IL7R-006, the present inventors also uncovered additional target sequences that increase exon 6 inclusion (listed in Table 1). These include two clusters of SM-ASOs, Cluster 1 (intron 5) and Cluster 2 (intron 6), and several other SM-ASOs, which increase exon 6 inclusion albeit less efficiently than lead SM-ASOs IL7R-005 and IL7R-006. The present inventors are currently refining the final target sequence for the newly discovered SM-ASOs to improve their efficiency.

This screen also uncovered several SM-ASOs that decrease exon 6 inclusion (seen as increased GFP expression in FIGS. 3B and 3C, and listed in Table 2). The latter are candidates for therapeutic intervention in immuno-oncology. Importantly, this approach identified new SM-ASO targets for autoimmunity and cancer to be tested in preclinical models.

Figure 4A:
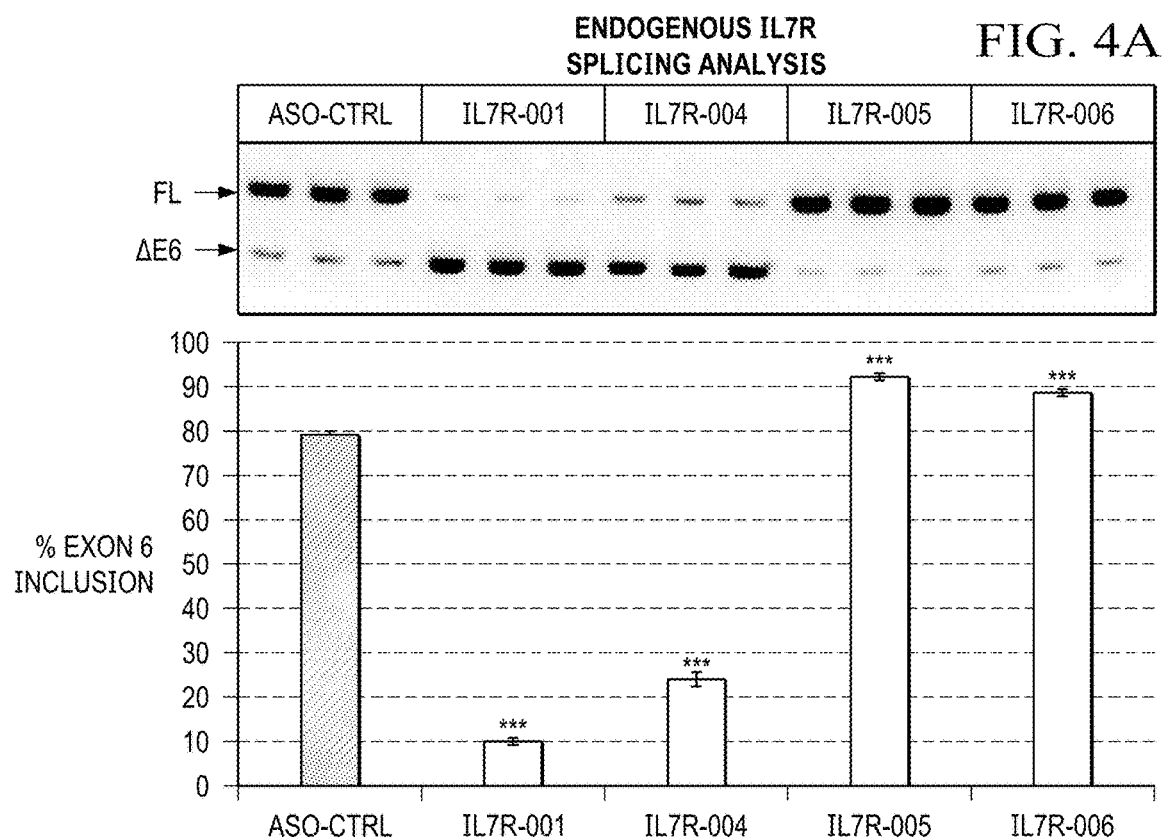
FIGS. 4A to 4D show the effects of selected SM-ASOs on expression of IL7R protein isoforms.
Figure 4B:
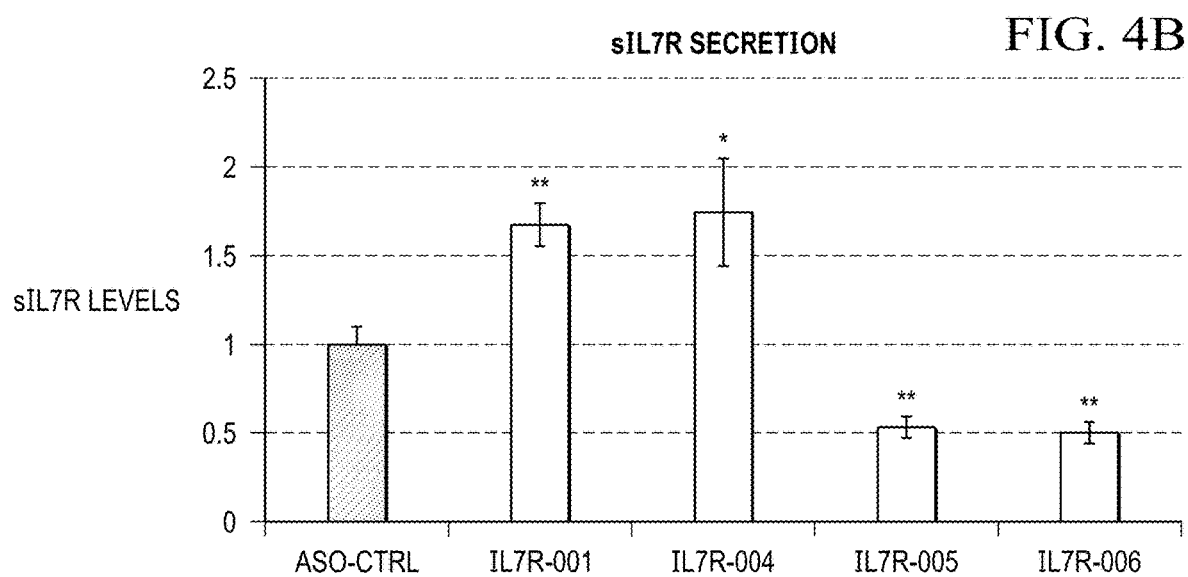
Figure 4C:
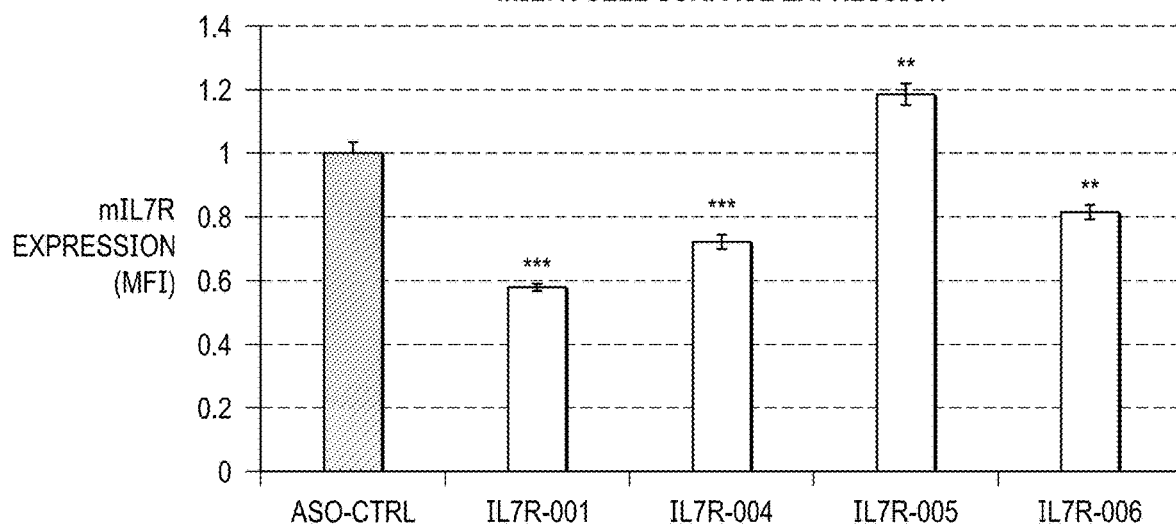
Figure 4D:
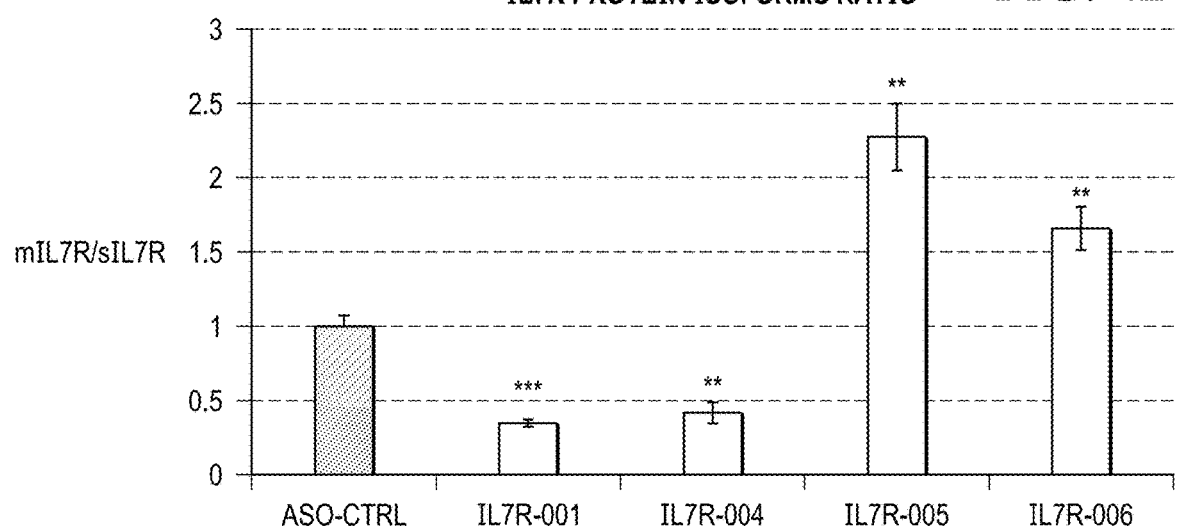

FIGS. 4A to 4D show the effects of selected SM-ASOs on expression of IL7R protein isoforms. HeLa cells were transfected with control (ASO-Ctrl) or experimental (IL7R-001, IL7R-004, IL7R-005 and IL7R-006) morpholino SM-ASOs using the Endo-Porter transfection system (Gene Tools) as before. FIG. 4A shows splicing analysis of exon 6 in transcripts from the endogenous IL7R gene. Total RNA was isolated from cells and percentage of exon 6 inclusion was determined by RT-PCR as before. FIG. 4B shows the quantification of soluble IL7R (sIL7R) secretion. Secretion of sIL7R was quantified by ELISA in supernatants collected from cells in panel A. Data are shown as average absorbance for experimental SM-ASOs normalized to control (ASO-Ctrl). FIG. 4C shows the quantification of cell surface expression of membrane-bound IL7R (mIL7R). Cell surface expression of mIL7R was determined by flow cytometry with IL7R staining in intact cells. Data are shown as mean fluorescence intensity (MFI) of IL7R staining normalized to control. FIG. 4D shows the ratio of IL7R protein isoforms expression. Ratio of mIL7R to sIL7R (mIL7R/sIL7R) was determined by dividing values of mIL7R cell surface expression (FIG. 4C) by sIL7R secretion (FIG. 4B). In all panels, statistical significance was assessed by two-tailed Student's t-test comparing experimental SM-ASOs versus control (*p<0.05, p<0.005, *p<0.0005).

These results demonstrate that SM-ASOs targeting sequences in IL7R exon 6 or intron 6 not only induce the desired outcome in exon 6 splicing but more importantly in the ratio of IL7R protein isoforms (mIL7R/sIL7R). Prominently, IL7R-005 and IL7R-006 decreased sIL7R levels with minimal impact on mIL7R cell surface expression. The latter is crucial for treatment of MS and autoimmunity, since inhibition of mIL7R expression or activity causes immunosuppression. The SM-ASOs IL7R-005 and IL7R-006 meet the first efficacy endpoint, which is to restore IL7R protein isoforms. Importantly, these SM-ASOs are predicted to be a safe and yet effective therapeutic drug for MS and other autoimmune diseases via mechanisms that prevent immunosuppression.

In addition, these analyses show that IL7R SM-ASOs that decreased exon 6 inclusion (IL7R-001 and IL7R-004), effectively increased sIL7R levels, meeting the first efficacy endpoint for a potential cancer immunotherapy. These SM-ASOs are predicted to enhance the power of the immune system to fight off and eradicate cancer cells.

Figure 5B:
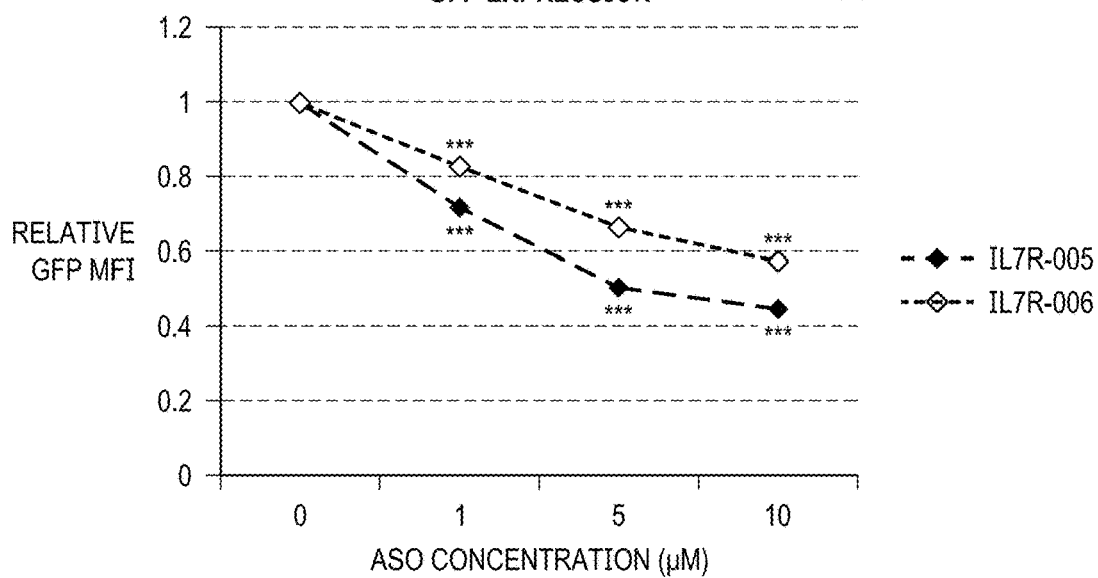
Figure 5C:
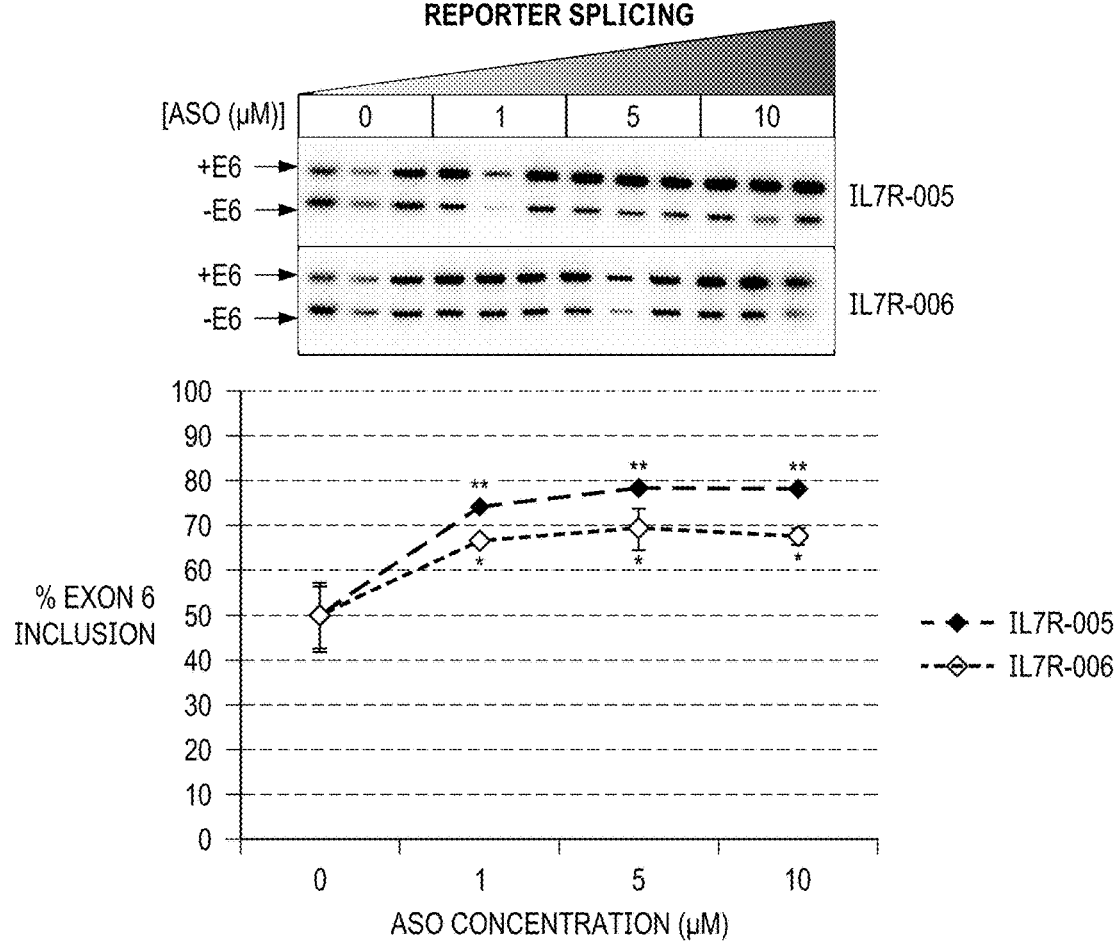
Figure 5D:
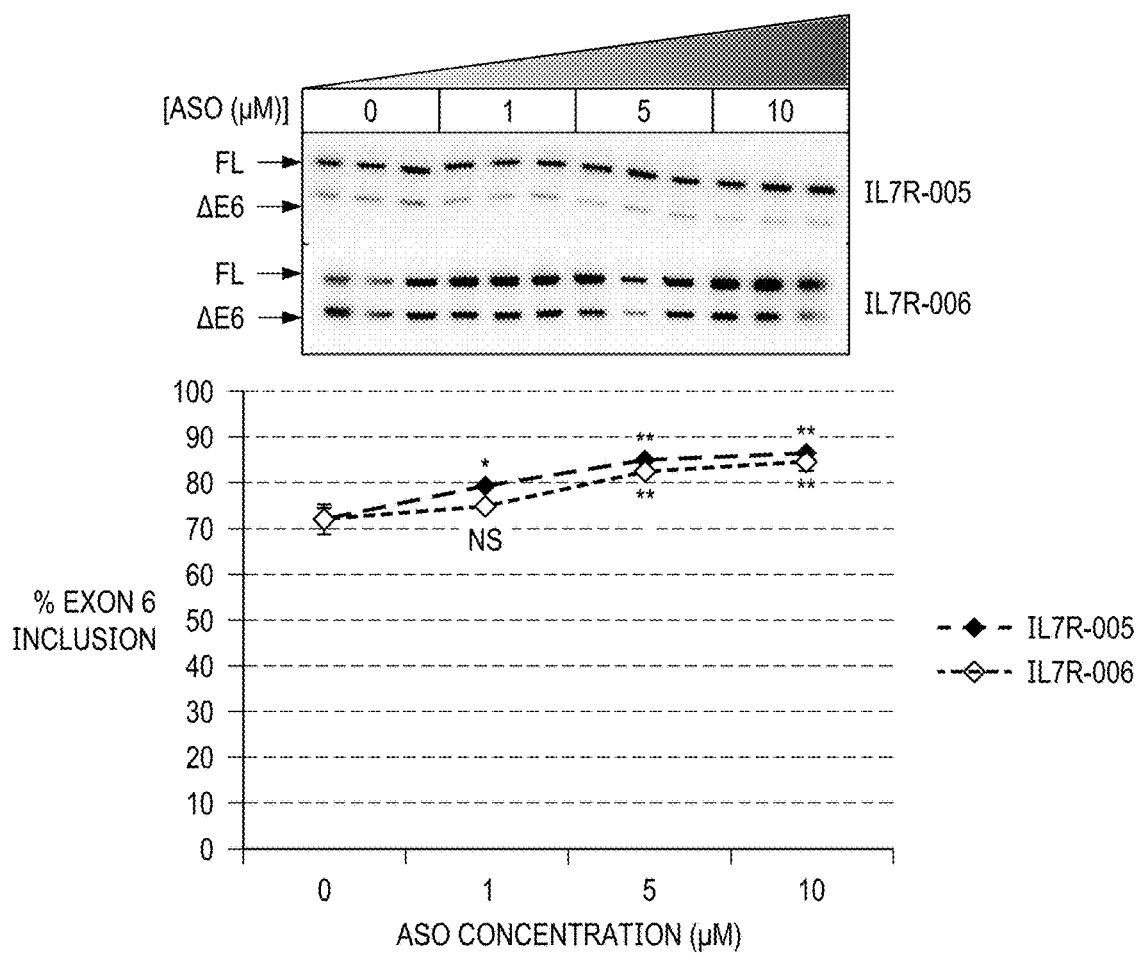

FIGS. 5A to 5D show the dose-response modulation of IL7R exon 6 splicing of lead SM-ASOs that reduce sIL7R. HeLa cells stably expressing the fluorescent reporter were transfected with increasing concentrations [0, 1, 5, and 10 µM] of control (ASO-Ctrl=0 µM) or experimental (IL7R-005 and IL7R-006) morpholino SM-ASOs as before. FIGS. 5A and 5B show analysis of GFP expression. GFP mean fluorescence intensity (MFI) was measured by flow cytometry as before. FIG. 5A shows representative histograms of GFP MFI for IL7R-005 at different concentrations, whereas FIG. 5B shows normalized GFP MFI as a function of SM-ASO concentration. FIGS. 5C and 5D show splicing analysis of IL7R exon 6 in transcripts from the reporter (FIG. 5C) or endogenous gene (FIG. 5D). The percentage of exon 6 inclusion in transcripts from the reporter or the endogenous gene was determined as before and is shown as a function of SM-ASOs concentration. In all panels, statistical significance was assessed by two-tailed Student's t-test comparing experimental concentrations versus control (*p<0.05, p<0.005, *p<0.0005).

Figure 6A:
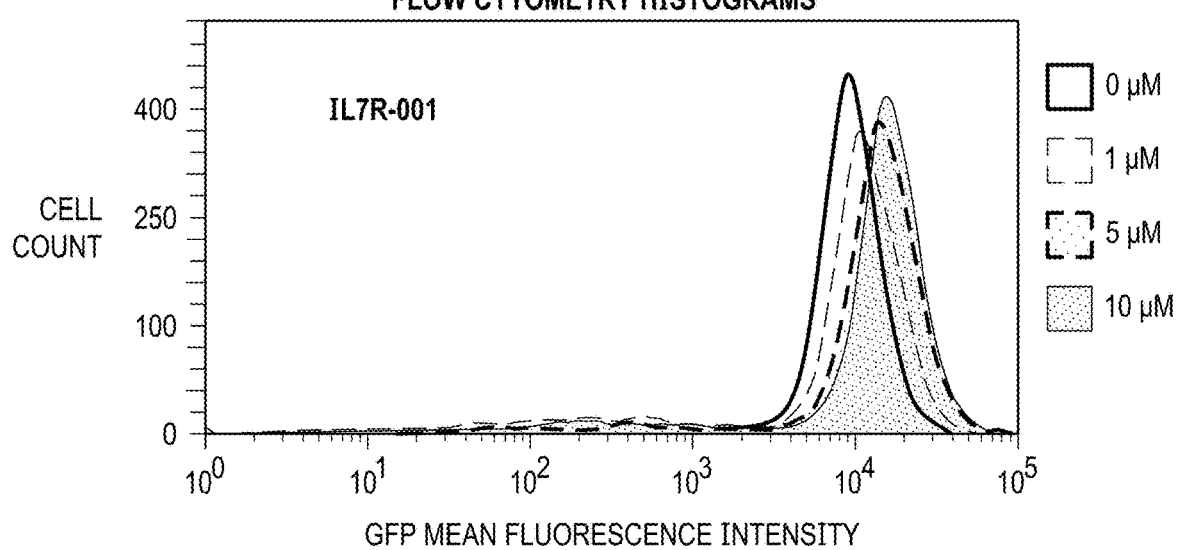
FIGS. 6A to 6D show the dose-response effects of lead SM-ASOs that increase sIL7R on modulation of IL7R exon 6 splicing.
Figure 6B:
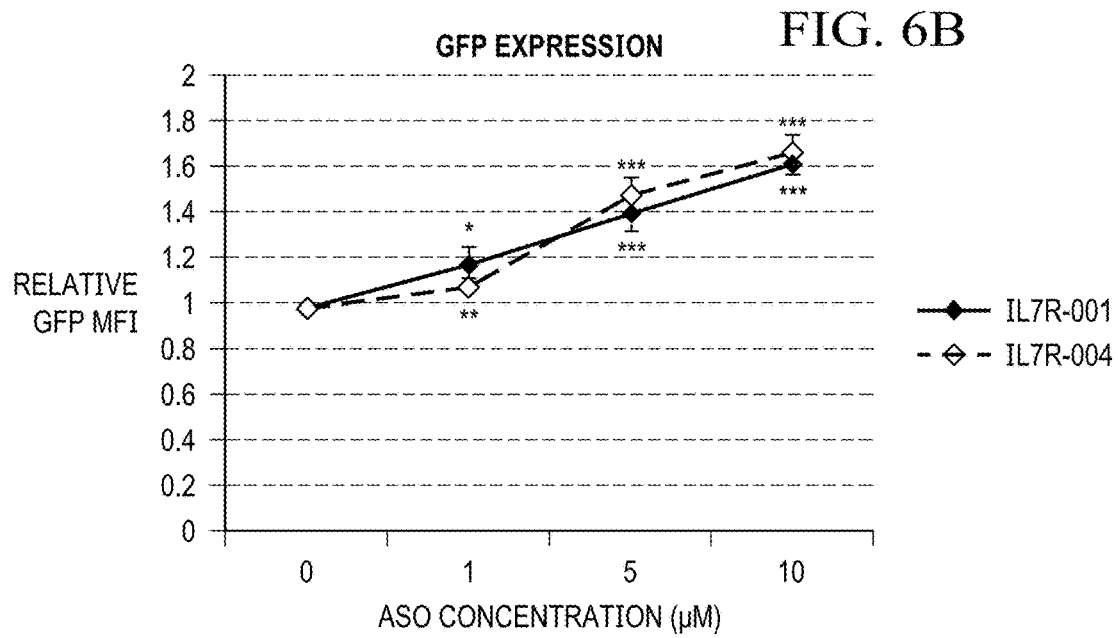
Figure 6C:
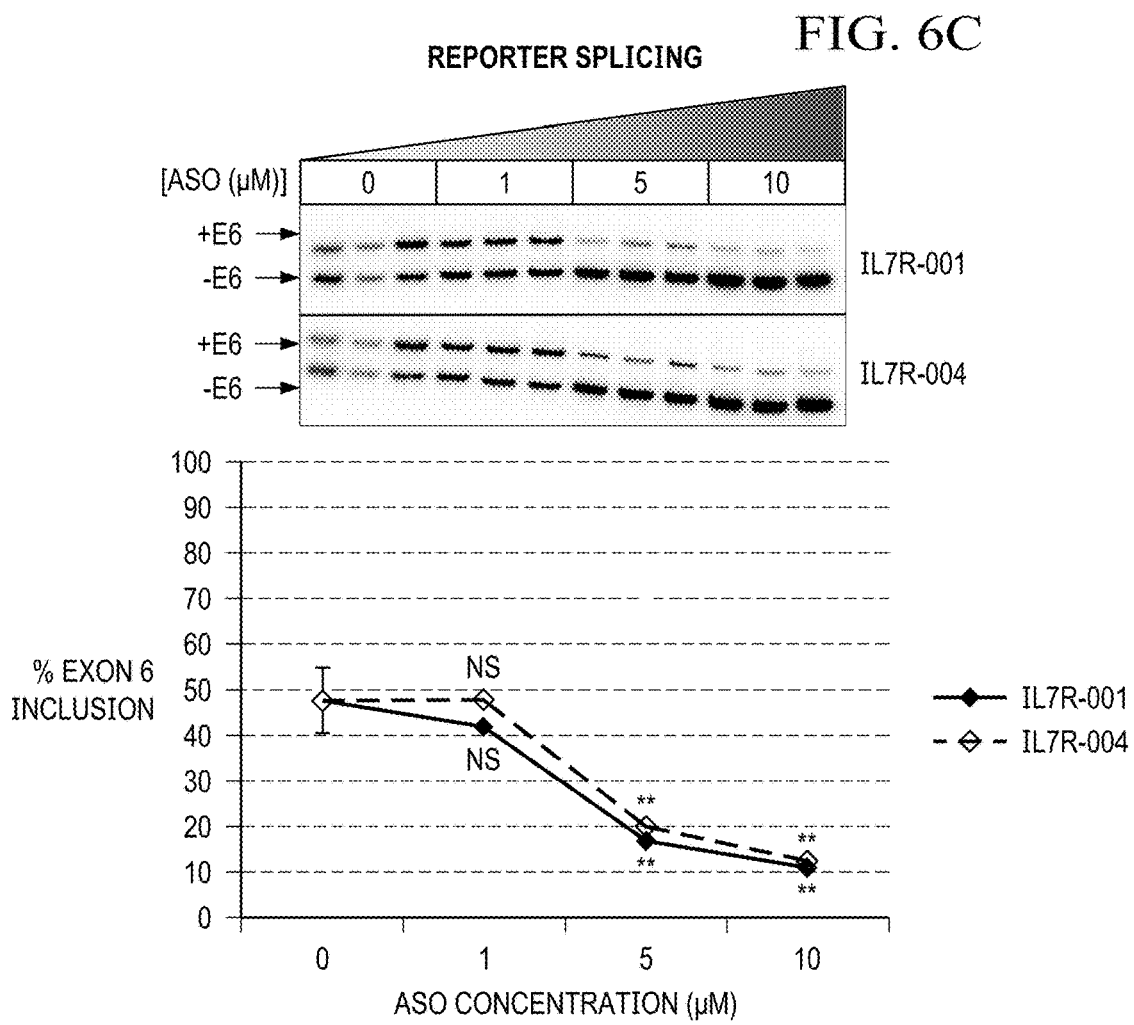
Figure 6D:
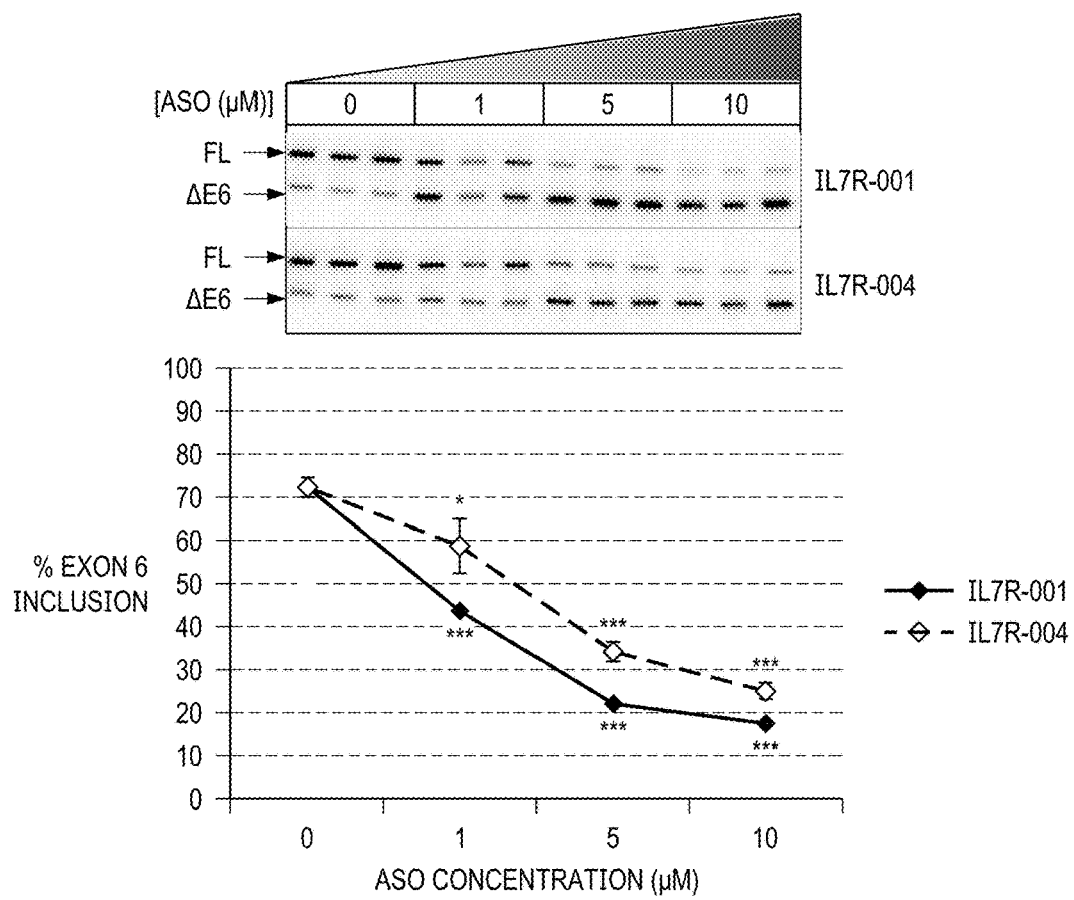

FIGS. 6A to 6D show the dose-response modulation of IL7R exon 6 splicing of lead SM-ASOs that increase sIL7R. HeLa cells stably expressing the fluorescent reporter were transfected with increasing concentrations [0, 1, 5, and 10 µM] of control (ASO-Ctrl=0 µM) or experimental (IL7R-001 and IL7R-004) morpholino SM-ASOs as before. FIGS. 6A and 6B show analysis of GFP expression. GFP mean fluorescence intensity (MFI) was measured by flow cytometry as before. FIG. 6A shows representative histograms of GFP MFI for IL7R-001 at different concentrations, whereas FIG. 6B shows normalized GFP MFI as a function of SM-ASO concentration. FIGS. 6C and 6D show splicing analysis of IL7R exon 6 in transcripts from the reporter (FIG. 6C) or endogenous gene (FIG. 6D). The percentage of exon 6 inclusion in transcripts from the reporter or the endogenous gene was determined as before and is shown as a function of SM-ASOs concentration. In all panels, statistical significance was assessed by two-tailed Student's t-test comparing experimental concentrations versus control (*p<0.05, p<0.005, *p<0.0005).

The analyses in FIGS. 5A to 5D and 6A to 6D demonstrate that IL7R exon 6 splicing can be fine-tuned in a dose-dependent manner by manipulating the dose of SM-ASOs used, and uncovered the minimal effective concentration for IL7R splicing modulation in cell culture. Importantly, these results could be used to extrapolate in vivo dosing in pre-clinical studies in nonhuman primates and clinical trials in humans. This dose-response analysis illustrates an example of the dose-responsiveness of lead SM-ASOs, and does not limit our applications to the range of concentrations tested.

Figure 7A:
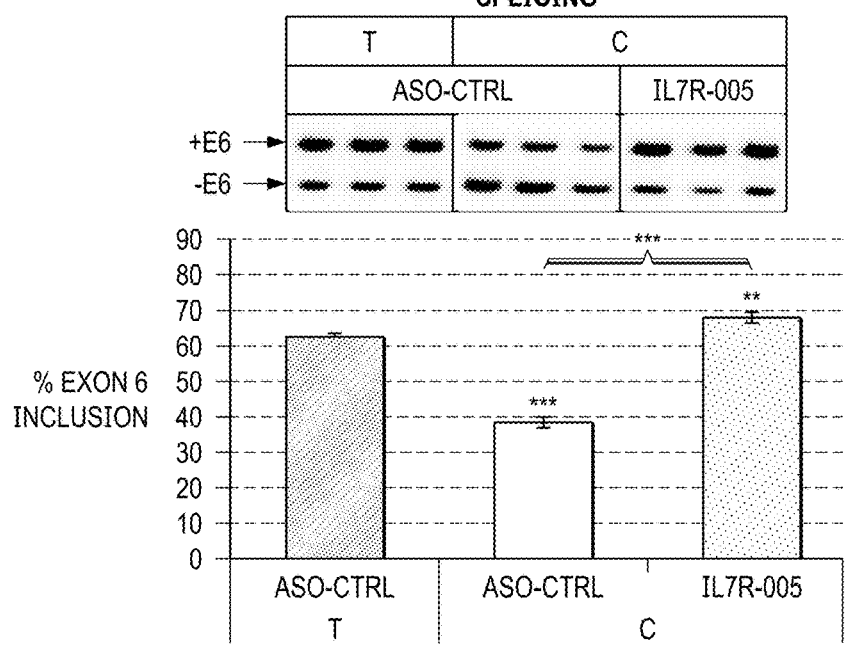
FIGS. 7A to 7B show correction by IL7R-005 of the effects of the genetic anomaly that increases exclusion of IL7R exon 6 and sIL7R levels in MS.
Figure 7B:
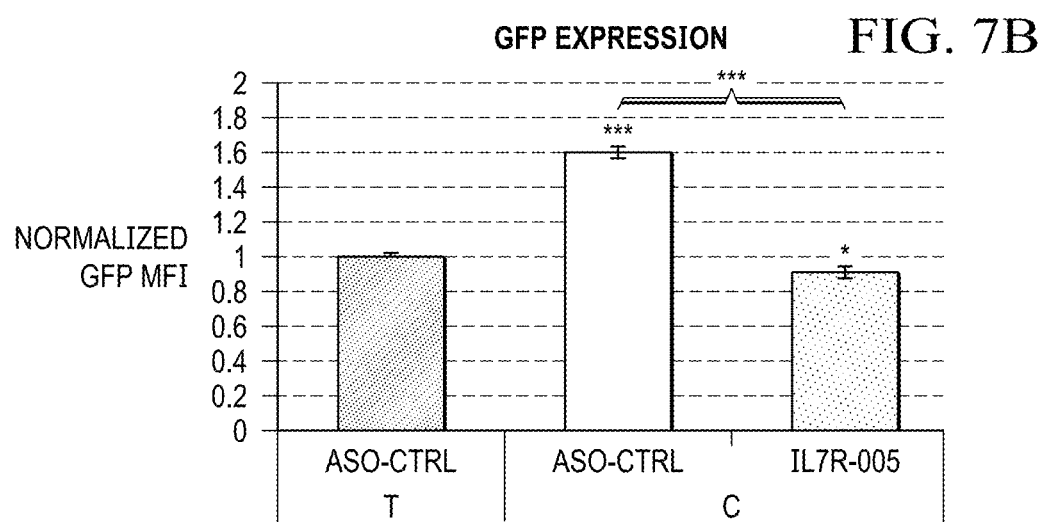

FIGS. 7A to 7B show correction by IL7R-005 of the abnormal exclusion of IL7R exon 6 driven by the MS-associated SNP rs6897932. Hela cells stably expressing versions of the GFP-IL7R reporter containing either the protective 'T' allele or the risk 'C' allele of the MS-associated variant rs6897932 in IL7R exon 6 were transfected with either control SM-ASO (ASO-Ctrl) or IL7R-005. FIG. 7A shows splicing analysis of IL7R exon 6 in transcripts from the GFP-IL7R reporter containing the alternative alleles of rs68978932 (C or T). Percentage exon 6 inclusion was determined by RT-PCR as before. FIG. 7B shows analysis of GFP expression in cells from FIG. 7A. GFP mean fluorescence intensity (MFI) was measured by flow cytometry as before, and is shown normalized to cells expressing the 'T' reporter treated with control SM-ASO. In all panels, statistical significance was assessed by two-tailed Student's t-test comparing experimental SM-ASOs versus control or as indicated (*p<0.05, p<0.005, *p<0.0005).

Previous studies by the present inventors and others found the risk 'C' allele of the genetic variant rs6897932 (C or T) in IL7R exon 6 to increase MS risk by enhancing exclusion of exon 6 and sIL7R levels (Gregory et al., 2007; Evsyukova et al., 2013; Hoe et al., 2010; Lundstrom et al., 2013). The analysis above demonstrates that IL7R-005, the lead SM-ASO for treatment of autoimmunity, restores the effects of the risk 'C' allele of rs6897932, which strongly supports the therapeutic potential of IL7R-005.

Thus, the present inventors have described compositions and methods for using antisense oligonucleotides to control alternative splicing of exon 6 of the Interleukin 7 receptor (IL7R) RNAs for therapeutic intervention in autoimmunity and cancer. These antisense oligonucleotides control splicing of IL7R exon 6 by blocking specific signals embedded in IL7R RNAs. These signals are specific sequences that determine the splicing outcome of IL7R exon 6. Further, specific sequences in IL7R RNAs to be blocked by antisense oligonucleotides to reduce sIL7R are listed in Table 1, including variations of these sequences, any portion of these sequences, or any nucleotides flanking these sequences that increase inclusion of IL7R exon 6, thus decreasing sIL7R secretion. Further, additional signals in IL7R RNAs to be blocked by antisense oligonucleotides to increase sIL7R are listed in Table 2, including variations of these sequences, any portion of these sequences, or any nucleotides flanking these sequences that decrease inclusion of IL7R exon 6, thus increasing sIL7R secretion. Blocking just a few nucleotides of these sequences can affect splicing of exon 6 because the actual element(s) that drives exclusion/inclusion is not the entire targeted sequence but usually a sequence of 4-8 nt within the targeted sequence. For example, an important sequence within the IL7R-005 target sequence is the last 5 nt UGGUC, thus, an ASO blocking just this 5 nt sequence or a few nt of this sequence might be sufficient to cause the desired effect. However, in order to maximize targeting specificity and efficiency for the functional sequence the oligonucleotide is often made to a longer complementary sequence. Finally, it is well known that it is possible to replace one or more bases in the antisense oligonucleotide to modify base-pairing while retaining high affinity, selectivity and efficient antisense activity for said target sequences. Depending on the length of the SM-ASO, non-limiting examples are those having 15, 20, or 25 nucleotides, which may have 70, 75, 80, 84, 85, 87, 88, 90, 92, 93, 94, 95, or 96, percent identity to any of the SEQ IDs in Tables 1 and 2, or portions thereof, either alone or in combination, fully or partially, or any biologically active permutation of these SEQ IDs for the treatment of autoimmune diseases, inflammatory diseases or cancer, respectively, or sequences complementary thereto, for use as a composition and in methods for reducing the expression of soluble IL7R by enhancing the inclusion of IL7R exon 6 for treatment of autoimmune and/or inflammatory diseases, or for enhancing the expression of soluble IL7R by reducing the inclusion of IL7R exon 6 for treatment of cancer. For a SM-ASO having 5, 10, 15, 20 or 25 nucleotides the mismatch may be, e.g., 1, 2, 3, 4, 5 or more mismatches.

TABLE 3

Summary of percent identity (% identity) with up to 8 mismatches for each of IL7R-005 and IL7R-006.

| mismatches | IL7R-005 (15 nt) percent identity | IL7R-006 (20 nt) percent identity | IL7R-001 (25 nt) percent identity | IL7R-004 (15 nt) percent identity |
|---|---|---|---|---|
| 0 | 100 | 100 | 100 | 100 |
| 1 | 93 | 95 | 96 | 93 |
| 2 | 87 | 90 | 92 | 87 |
| 3 | 80 | 85 | 88 | 80 |
| 4 | 73 | 80 | 84 | 73 |
| 5 | 67 | 75 | 80 | 67 |
| 6 | 60 | 70 | 76 | 60 |
| 7 | 53 | 65 | 72 | 53 |
| 8 | 47 | 60 | 68 | 47 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, "without limitation", "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, or AIA 35 U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Allcock, R. J., Williams, J. H., and Price, P. (2001). The central MHC gene, BAT1, may encode a protein that down-regulates cytokine production. Genes Cells 6, 487-494. 974.

Anderson, C. A., Boucher, G., Lees, C. W., Franke, A., D'Amato, M., Taylor, K. D., Lee, J. C., Goyette, P., Imielinski, M., Latiano, A., et al. (2011). Meta-analysis identifies 29 additional ulcerative colitis risk loci, increasing the number of confirmed associations to 47. Nature genetics 43, 246-252.

V. Badot et al., Rheumatoid arthritis synovial fibroblasts produce a soluble form of the interleukin-7 receptor in response to pro-inflammatory cytokines. J Cell Mol Med 15, 2335-2342 (2011).

V. Badot et al., Serum soluble interleukin 7 receptor is strongly associated with lupus nephritis in patients with systemic lupus erythematosus. Ann Rheum Dis 72, 453-456 (2013).

Barrett, J. C., Clayton, D. G., Concannon, P., Akolkar, B., Cooper, J. D., Erlich, H. A., Julier, C., Morahan, G., Nerup, J., Nierras, C., et al. (2009). Genome-wide association study and meta-analysis find that over 40 loci affect risk of type 1 diabetes. Nature genetics 41, 703-707.

Cheong, Allcock, R. J., Eerligh, P., Witt, C. S., Christiansen, F. T., McCann, V., and Price, P. (2001). Localization of central MHC genes influencing type I diabetes. Human immunology 62, 1363-1370.

Degli-Esposti, M. A., Leelayuwat, C., and Dawkins, R. L. (1992). Ancestral haplotypes carry haplotypic and haplospecific polymorphisms of BAT1: possible relevance to autoimmune disease. Eur J Immunogenet 19, 121-127.

Evsyukova, I., Bradrick, S. S., Gregory, S. G., and Garcia-Blanco, M. A. (2013). Cleavage and polyadenylation specificity factor 1 (CPSF1) regulates alternative splicing of interleukin 7 receptor (IL7R) exon 6. RNA 19, 103-115.

Galarza-Munoz, G., Briggs, F. B., Evsyukova, I., Schott-Lerner, G., Kennedy, E. M., Nyanhete, T., Wang, L., Bergamaschi, L., Widen, S. G., Tomaras, G. D., et al. (2017). Human Epistatic Interaction Controls IL7R Splicing and Increases Multiple Sclerosis Risk. Cell 169, 72-84 e13.

Gregory, S. G., Schmidt, S., Seth, P., Oksenberg, J. R., Hart, J., Prokop, A., Caillier, S. J., Ban, M., Goris, A., Barcellos, L. F., et al. (2007). Interleukin 7 receptor alpha chain (IL7R) shows allelic and functional association with multiple sclerosis. Nature genetics 39, 1083-1091.

Kilding, R., Iles, M. M., Timms, J. M., Worthington, J., and Wilson, A. G. (2004). Additional genetic susceptibility for rheumatoid arthritis telomeric of the DRB1 locus. Arthritis and rheumatism 50, 763-769.

B. R. Lauwerys, S. N. Husson, A. L. Maudoux, V. Badot, F. A. Houssiau, sIL7R concentrations in the serum reflect disease activity in the lupus kidney. Lupus Sci Med 1, e000036 (2014).

Lundstrom, W., Highfill, S., Walsh, S. T., Beq, S., Morse, E., Kockum, I., Alfredsson, L., Olsson, T., Hillert, J., and Mackall, C. L. (2013). Soluble IL7Ralpha potentiates IL-7 bioactivity and promotes autoimmunity. Proceedings of the National Academy of Sciences of the United States of America 110, E1761-1770.

Maraskovsky, E., Teepe, M., Morrissey, P. J., Braddy, S., Miller, R. E., Lynch, D. H., and Peschon, J. J. (1996). Impaired survival and proliferation in IL-7 receptor-deficient peripheral T cells. Journal of immunology 157, 5315-5323.

F. C. McKay et al., Haplotypes of the interleukin 7 receptor alpha gene are correlated with altered expression in whole blood cells in multiple sclerosis. Genes Immun 9, 1-6 (2008).

P. Monti, C. Brigatti, M. Krasmann, A. G. Ziegler, E. Bonifacio, Concentration and activity of the soluble form of the interleukin-7 receptor alpha in type 1 diabetes identifies an interplay between hyperglycemia and immune function. Diabetes 62, 2500-2508 (2013).

Nakamura, M., Nishida, N., Kawashima, M., Aiba, Y., Tanaka, A., Yasunami, M., Nakamura, H., Komori, A., Nakamuta, M., Zeniya, M., et al. (2012). Genome-wide association study identifies TNFSF15 and POU2AF1 as susceptibility loci for primary biliary cirrhosis in the Japanese population. American journal of human genetics 91, 721-728.

Okamoto, K., Makino, S., Yoshikawa, Y., Takaki, A., Nagatsuka, Y., Ota, M., Tamiya, G., Kimura, A., Bahram, S., and Inoko, H. (2003). Identification of I kappa B L as the second major histocompatibility complex-linked susceptibility locus for rheumatoid arthritis. American journal of human genetics 72, 303-312.

Paternoster, L., Standl, M., Chen, C. M., Ramasamy, A., Bonnelykke, K., Duijts, L., Ferreira, M. A., Alves, A. C., Thyssen, J. P., Albrecht, E., et al. (2012). Meta-analysis of genome-wide association studies identifies three new risk loci for atopic dermatitis. Nature genetics 44, 187-192.

Peschon, J. J., Morrissey, P. J., Grabstein, K. H., Ramsdell, F. J., Maraskovsky, E., Gliniak, B. C., Park, L. S., Ziegler, S. F., Williams, D. E., Ware, C. B., et al. (1994). Early lymphocyte expansion is severely impaired in interleukin 7 receptor-deficient mice. J Exp Med 180, 1955-1960.

Price, P., Wong, A. M., Williamson, D., Voon, D., Baltic, S., Allcock, R. J., Boodhoo, A., and Christiansen, F. T.

(2004). Polymorphisms at positions −22 and −348 in the promoter of the BAT1 gene affect transcription and the binding of nuclear factors. Human molecular genetics 13, 967-974.

Puel, A., Ziegler, S. F., Buckley, R. H., and Leonard, W. J. (1998). Defective IL7R expression in T(−)B(+)N K(+) severe combined immunodeficiency. Nature genetics 20, 394-397.

Quinones-Lombrana, A., Lopez-Soto, A., Ballina-Garcia, F. J., Alperi-Lopez, M., Queiro-Silva, R., Lopez-Vazquez, A., Lopez-Larrea, C., and Gonzalez, S. (2008). BAT1 promoter polymorphism is associated with rheumatoid arthritis susceptibility. J Rheumatol 35, 741-744.

Roifman, C. M., Zhang, J., Chitayat, D., and Sharfe, N. (2000). A partial deficiency of interleukin-7R alpha is sufficient to abrogate T-cell development and cause severe combined immunodeficiency. Blood 96, 2803-2807.

Todd, J. A., Walker, N. M., Cooper, J. D., Smyth, D. J., Downes, K., Plagnol, V., Bailey, R., Nejentsev, S., Field, S. F., Payne, F., et al. (2007). Robust associations of four new chromosome regions from genome-wide analyses of type 1 diabetes. Nature genetics 39, 857-864.

Wong, A. M., Allcock, R. J., Cheong, K. Y., Christiansen, F. T., and Price, P. (2003). Alleles of the proximal promoter of BAT1, a putative anti-inflammatory gene adjacent to the TNF cluster, reduce transcription on a disease-associated MHC haplotype. Genes Cells 8, 403-412.

---

What is claimed is:

1. A method of treating a disease or disorder with elevated levels of a soluble isoform of an interleukin 7 receptor (sIL7R) in a subject in need thereof, the method comprising: administering an effective amount of a composition comprising a splice-modulating antisense oligonucleotide (SM-ASO) that specifically binds to a sequence of the Interleukin-7 receptor (IL7R) pre-mRNA and increases inclusion of exon 6 in IL7R pre-mRNAs and decreases expression of the soluble isoform of IL7R (sIL7R).

2. The method of claim 1, wherein the SM-ASO specifically binds to a sequence in IL7R pre-mRNA in at least one of the group consisting of an exonic splicing silencer (ESS) and/or an intronic splicing silencer (ISS), thereby enhancing inclusion of exon 6 in IL7R pre-mRNAs, and reducing expression of sIL7R.

3. The method of claim 1, wherein at least one or more nucleotide(s) in the SM-ASO contains a non-naturally occurring modification comprising modifications or substitutions of: (1) the ribose or other sugar units, (2) bases, or (3)

the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides0), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), a non-naturally occurring modification to the nucleotide bases and any combinations of one or more of any of the foregoing.

4. The method of claim 1, wherein the composition further comprises a pharmaceutically acceptable excipient, salts, or carrier.

5. The method of claim 1, wherein the disease or condition is an autoimmune disorder selected from at least one of the following: multiple sclerosis, type I diabetes, rheumatoid arthritis, systemic lupus erythematosus, atopic dermatitis, ankylosing spondylitis, primary biliary cirrhosis, or inflammatory bowel syndromes such as ulcerative colitis and Crohn's disease, or any other conditions where sIL7R is elevated when compared to a normal subject without a disease or condition.

6. The method of claim 1, wherein the disease or condition is an inflammatory disease or condition.

7. The method of claim 1, further comprising a combination therapy of the SM-ASO and one or more active agents effective for treating a disease or condition that is an autoimmune or an inflammatory disease selected from at least one of: mitoxatrone, interferon beta-1a, PEG-interferon beta-1a, azathioprine, fingolimod, natalizumab, methylprednisolone, or ocrelizumab.

8. The method of claim 1, further comprising the steps of obtaining cells from the patient and modifying the cells to transiently or permanently express the SM-ASO that specifically binds to a sequence of the Interleukin-7 receptor (IL7R) pre-mRNA that influences splicing of exon 6.

9. The method of claim 1, further comprising generating a vector that expresses the SM-ASO that specifically binds to a sequence of the Interleukin-7 receptor (IL7R) pre-mRNA that influences splicing of exon 6 for use in gene therapy, and treating the patient with the vector.

10. A method of increasing inclusion of exon 6 of an Interleukin-7 receptor (IL7R) pre-mRNA, the method comprising: contacting a splice modulating antisense oligonucleotide (SM-ASO) that specifically binds to a sequence of the Interleukin-7 receptor (IL7R) pre-mRNA and increases inclusion of exon 6 in IL7R pre-mRNAs and decreases expression of the soluble isoform of IL7R (sIL7R).

11. The method of claim 10, wherein the SM-ASO specifically binds to a sequence in IL7R pre-mRNA in at least one of the group consisting of an exonic splicing silencer (ESS) and/or an intronic splicing silencer (ISS), thereby enhancing inclusion of exon 6 in IL7R pre-mRNAs, and reducing expression of sIL7R.

12. The method of claim 10, wherein at least one or more nucleotide(s) in the SM-ASO contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and any combinations of two or more of any of the foregoing.

13. The method of claim 10, wherein at least one or more nucleotide(s) in the SM-ASO contains a non-naturally occurring modification to the nucleotide bases.

14. The method of claim 10, wherein the composition further comprises a pharmaceutically acceptable excipient, salts, or carrier.

15. The method of claim 10, wherein the autoimmune disorder is selected from at least one of the following: multiple sclerosis, type I diabetes, rheumatoid arthritis, systemic lupus erythematosus, atopic dermatitis, ankylosing spondylitis, primary biliary cirrhosis, or inflammatory bowel syndromes such as ulcerative colitis and Crohn's disease, or any other conditions where sIL7R is elevated.

16. A vector that expresses a nucleic acid comprising an oligonucleotide that is an antisense oligonucleotide (ASO), or a splice-modulating antisense oligonucleotide (SM-ASO), that specifically binds a sequence in the Interleukin-7 receptor (IL7R) pre-mRNA that influences splicing of exon 6, wherein the SM-ASO increases inclusion of exon 6 in IL7R pre-mRNAs and decreases expression of the soluble isoform of IL7R (sIL7R).

17. The vector of claim 16, wherein the vector is a viral vector or a plasmid.

18. A method of treating multiple sclerosis in a subject in need thereof, the method comprising: administering an effective amount of a composition comprising a splice modulating antisense oligonucleotide (SM-ASO) that specifically binds a sequence of an Interleukin-7 receptor (IL7R) pre-mRNA increases inclusion of exon 6 in IL7R pre-mRNAs and decreases expression of the soluble isoform of IL7R (sIL7R) in a pharmaceutically acceptable excipient.

19. The method of claim 18, further comprising a combination therapy of the SM-ASO and one or more active agents effective for treating multiple sclerosis disease.

20. The method of claim 19, wherein the one or more agents for treating multiple sclerosis are selected from mitoxatrone, interferon beta-1a, PEG-interferon beta-1a, azathioprine, fingolimod, natalizumab, methylprednisolone, or ocrelizumab.

21. The method of claim 18, wherein the at least one or more nucleotide(s) in the oligonucleotide contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, alkyl silyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and combinations of two or more of any of the foregoing; in another aspect, at least one or more nucleotide(s) in the oligonucleotide contains a non-naturally occurring modification to the nucleotide bases.

* * * * *